US010660530B2

(12) United States Patent
Montgomery et al.

(10) Patent No.: US 10,660,530 B2
(45) Date of Patent: May 26, 2020

(54) DETERMINING CHANGES TO AUTOREGULATION

(71) Applicant: Covidien LP, Mansfield, MA (US)

(72) Inventors: Dean Montgomery, Edinburgh (GB); Paul S. Addison, Edinburgh (GB)

(73) Assignee: COVIDIEN LP, Mansfield, MA (US)

(*) Notice: Subject to any disclaimer, the term of this patent is extended or adjusted under 35 U.S.C. 154(b) by 146 days.

(21) Appl. No.: 15/962,486

(22) Filed: Apr. 25, 2018

(65) Prior Publication Data
US 2019/0328242 A1 Oct. 31, 2019

(51) Int. Cl.
*A61B 5/02* (2006.01)
*A61B 5/0205* (2006.01)
(Continued)

(52) U.S. Cl.
CPC .......... *A61B 5/0205* (2013.01); *A61B 5/7246* (2013.01); *A61B 5/7275* (2013.01);
(Continued)

(58) Field of Classification Search
CPC ..... A61B 5/0205; A61B 5/743; A61B 5/7246; A61B 5/7275; A61B 5/7278; A61B 5/14551; A61B 5/0075; A61B 5/021
See application file for complete search history.

(56) References Cited

U.S. PATENT DOCUMENTS 4,688,577 A 8/1987 Bro
5,579,774 A 12/1996 Miller et al.
(Continued)

FOREIGN PATENT DOCUMENTS

CN 100399990 A 12/2006
DE 10331027 A1 1/2005
(Continued)

OTHER PUBLICATIONS

Chuan et al., "Is cerebrovascular autoregulation associated with outcomes after major noncardiac surgery? A prospective observational pilot study," Acta Anaesthesiol Scand., Aug. 5, 2018, 10 pp.
(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

In some examples, a device includes processing circuitry configured to determine a set of correlation coefficient values for values of first and second physiological parameters. The processing circuitry is further configured to determine that the first physiological parameter changes rapidly in a particular time period. The processing circuitry is configured to select a correlation coefficient value associated with the particular time period and determine an updated value of the selected correlation coefficient value in response to determining that the first physiological parameter changes rapidly in a particular time period. The processing circuitry is further configured to determine an estimate of a limit of autoregulation of the patient based on the set of correlation coefficient values and the updated value. The processing circuitry is configured to determine an autoregulation status based on the estimate of the limit of autoregulation and output, for display, an indication of the autoregulation status.

20 Claims, 8 Drawing Sheets

(51) Int. Cl.
*A61B 5/00* (2006.01)
*A61B 5/021* (2006.01)
*A61B 5/1455* (2006.01)

(52) U.S. Cl.
CPC ............ *A61B 5/7278* (2013.01); *A61B 5/743* (2013.01); *A61B 5/0075* (2013.01); *A61B 5/021* (2013.01); *A61B 5/14551* (2013.01)

(56) References Cited

U.S. PATENT DOCUMENTS

| | | |
|---|---|---|
| 6,438,399 B1 | 8/2002 | Kurth |
| 6,599,251 B2 | 7/2003 | Chen et al. |
| 6,875,176 B2 | 4/2005 | Mourad et al. |
| 7,532,919 B2 | 5/2009 | Soyemi et al. |
| 7,744,541 B2 | 6/2010 | Baruch et al. |
| 7,998,075 B2 | 8/2011 | Ragauskas et al. |
| 8,057,398 B2 | 11/2011 | Mcnames et al. |
| 8,062,224 B2 | 11/2011 | Ragauskas et al. |
| 8,211,022 B2 | 7/2012 | Lo et al. |
| 8,366,627 B2 | 2/2013 | Kashif et al. |
| 8,433,384 B2 | 4/2013 | Bechtel et al. |
| 8,512,260 B2 | 8/2013 | Grudic et al. |
| 8,556,811 B2 | 10/2013 | Brady |
| 8,852,094 B2 | 10/2014 | Al-ali et al. |
| 9,192,330 B2 | 11/2015 | Lin et al. |
| 9,861,317 B2 | 1/2018 | Ochs |
| 2002/0099295 A1 | 7/2002 | Gil et al. |
| 2003/0219797 A1 | 11/2003 | Zhao et al. |
| 2009/0326386 A1 | 12/2009 | Sethi et al. |
| 2010/0030054 A1 | 2/2010 | Baruch et al. |
| 2011/0105912 A1 | 5/2011 | Widman et al. |
| 2011/0201962 A1* | 8/2011 | Grudic .................... A61B 5/021 600/561 |
| 2012/0004517 A1 | 1/2012 | Starr et al. |
| 2012/0253211 A1 | 10/2012 | Brady et al. |
| 2013/0144140 A1 | 6/2013 | Frederick et al. |
| 2013/0190632 A1 | 7/2013 | Baruch et al. |
| 2014/0073888 A1 | 3/2014 | Kim |
| 2014/0278285 A1 | 9/2014 | Marmarelis et al. |
| 2015/0230758 A1 | 8/2015 | Ochs |
| 2016/0081563 A1 | 3/2016 | Wiard et al. |
| 2016/0106372 A1* | 4/2016 | Addison ............... A61B 5/7221 600/324 |
| 2016/0162786 A1 | 6/2016 | Grudic et al. |
| 2016/0220115 A1 | 8/2016 | Fisher et al. |
| 2016/0324425 A1 | 11/2016 | Addison et al. |
| 2016/0345913 A1* | 12/2016 | Montgomery ....... A61B 5/7275 |
| 2016/0367197 A1* | 12/2016 | Addison ............. A61B 5/02028 |
| 2017/0105631 A1 | 4/2017 | Addison et al. |
| 2018/0014791 A1 | 1/2018 | Montgomery et al. |
| 2018/0338731 A1* | 11/2018 | Addison ................ G16H 50/20 |

FOREIGN PATENT DOCUMENTS

| | | |
|---|---|---|
| RU | 2465829 C1 | 11/2012 |
| WO | WO 2016015057 A1 | 1/2016 |

OTHER PUBLICATIONS

Ameloot et al., "An observational near-infrared spectroscopy study on cerebral autoregulation in post-cardiac arrest patients: Time to drop 'one-size-fits-all' hemodynamic targets?," Resuscitation 90, 121-126, Jan. 2015.

Brady, MD, et al., "Monitoring Cerebrovascular Autoregulation Refining care goals in the ICU," Apr. 21, 2009, 15 pp.

Brady, MD et al., "Real-time continuous monitoring of cerebral blood flow autoregulation using near-infrared spectroscopy in patients undergoing cardiopulmonary bypass," Stroke 41, pp. 1951-1956, Feb. 2010.

Brady, MD et al., "A Dynamic Association Between Cavopulmonary Shunt Pressure and Cerebrovascular Autoregulation in an Infant With Congenital Heart Disease and Intracranial Hemorrhage," J. Cardiothorac. Vasc. Anesth. Vo. 23, No. 2, pp. 215-218; Apr. 2009.

Brady, MD et al., "Continuous Measurement of Autoregulation by Spontaneous Fluctuations in Cerebral Perfusion Pressure: Comparison of 3 Methods," Stroke. 39, pp. 2531-2537; Sep. 2008.

Brady, MD et al., "Continuous Monitoring of Cerebrovascular Pressure Reactivity After Traumatic Brain Injury in Children," Pediatrics 124, e1205-e1212, Dec. 2009.

Brady, MD et al., "Continuous Time-Domain Analysis of Cerebrovascular Autoregulation Using Near-infrared Spectroscopy," Stroke 38, pp. 2818-2825; Oct. 2007.

Brady, MD et al., "Monitoring Cerebral Blood Flow Pressure Autoregulation in Pediatric Patients During Cardiac Surgery," Stroke 41, 1957-1962, Sep. 2010.

Brady, MD et al., "Noninvasive Autoregulation Monitoring With and Without Intracranial Pressure in the Naïve Piglet Brain," Anesth. Analg. vol. 111, No. 1, 191-195; Jul. 2010.

Budohoski, MD et al., "Bilateral Failure of Cerebral Autoregulation is Related to Unfavorable Outcome After Subarachnoid Hemorrhage," Neurocrit. Care 22, 65-73, Jul. 2014.

Budohoski, MD, et al., "The Relationship Between Cerebral Blood Flow Autoregulation and Cerebrovascular Pressure Reactivity After Traumatic Brain Injury," Neurosurgery 71, pp. 652-660 May 2012.

Calviere et al., "Prediction of Delayed Cerebral Ischemia After Subarachnoid Hemorrhage Using Cerebral Blood Flow Velocities and Cerebral Autoregulation Assessment," Neurocrit. Care, Feb. 2015.

Czosnyka, PhD, et al., "Intracranial pressure: More Than a Number," Neurosurg. Focus 22, E10, May 2007.

Czosnyka, PhD, et al., "Monitoring of Cerebrovascular Autoregulation: Facts, myths, and missing links," Neurocrit. Care 10, 373-386, Jan. 2009.

Czosnyka, PhD, et al., "Monitoring of Cerebral Autoregulation in Head-Injured Patients," Stroke. 27, 1829-1834, Oct. 1996.

Depreitere et al., "Pressure autoregulation monitoring and cerebral perfusion pressure target recommendation in patients with severe traumatic brain injury based on minute-by-minute monitoring data," J. Neurosurg. 120, pp. 1451-1457, Apr. 2014.

Dias et al., "Kidney-Brain Link in Traumatic Brain Injury Patients? A preliminary report," Neurocrit. Care, Oct. 2014, 12 pp.

Dias et al., "Optimal Cerebral Perfusion Pressure Management at Bedside: A Single-Center. Pilot Study," Neurocrit. Care, Jan. 2015, 13 pp.

Diedler, MD et al., "The Limitations of Near-Infrared Spectroscopy to Assess CerebrovascularR: The Role of Slow Frequency Oscillations," Anesth. Analg. vol. 113 No. 4, pp. 849-857, Oct. 2011.

Donnelly et al., "Further understanding of cerebral autoregulation at the bedside: possible implications for future therapy," Expert Rev. Neurother. 15, pp. 169-185, Jan. 2015.

Eide, MD, PhD., et al. "Pressure-derived versus pressure wave amplitude-derived indices of cerebrovascular pressure reactivity in relation to early clinical state and 12-month outcome following aneurysmal subarachnoid hemorrhage," J. Neurosurg. 116, pp. 961-971, May 2012.

Gilmore et al., "Relationship between cerebrovascular dysautoregulation and arterial blood pressure in the premature infant," J. Perinatol. 31, pp. 722-729, Mar. 2011.

Hori et al., "Effect of carotid revascularization on cerebral autoregulation in combined cardiac surgery," Eur. J. Cardio-Thoracic Surg., Feb. 2015,7 pp.

Howells et al., "An optimal frequency range for assessing the pressure reactivity index in patients with traumatic brain injury," J. Clin. Monit. Comput., pp. 97-105, Mar. 2014.

Howlett et al., "Cerebrovascular autoregulation and neurologic injury in neonatal hypoxic-ischemic encephalopathy," Pediatr. Res. vol. 74, No. 5, pp. 525-535, Nov. 2013.

Jaeger, MD et al., "Effects of cerebrovascular pressure reactivity-guided optimization of cerebral perfusion pressure on brain tissue oxygenation after traumatic brain injury," Crit. Care Med. vol. 38, No. 5, pp. 1343-1347, May 2010.

Jaeger, MD, et al., "Continuous monitoring of cerebrovascular autoregulation after subarachnoid hemorrhage by brain tissue oxy-

(56) References Cited

OTHER PUBLICATIONS gen pressure reactivity and its relation to delayed cerebral infarction," Stroke 38, pp. 981-986, Apr.-May 2007.
Kvandal et al., "Impaired cerebrovascular reactivity after acute traumatic brain injury can be detected by wavelet phase coherence analysis of the intracranial and arterial blood pressure signals," J. Clin. Monit. Comput. 27, pp. 375-383, May 2013.
Laflam et al., "Shoulder Surgery in the Beach Chair Position Is Associated with Diminished Cerebral Autoregulation but No Differences in Postoperative Cognition or Brain Injury Biomarker Levels Compared with Supine Positioning," Anesth. Analg. vol. 120, No. 1, pp. 176-185, Jan. 2015.
Lang MD, PhD, et al., "A Review of Cerebral Autoregulation: Assessment and Measurements," Aust. Anaesth. 161-172, 2005, (Applicant points out, in accordance with MPEP 609.04(a), that the year of publication, 2005, is sufficiently earlier than the effective U.S. filing date, Mar. 5, 2018, so that the particular month of publication is not in issue.).
Lang et al., "Short pressure reactivity index versus long pressure reactivity index in the management of traumatic brain injury," J. Neurosurg. vol. 122, pp. 588-594, Mar. 2015.
Lang et al., "Continuous monitoring of cerebrovascular autoregulation: a validation study," J. Neurol. Neurosurg. Psychiatry 72, pp. 583-586, Jan. 2002.
Lee et al., "A pilot study of cerebrovascular reactivity autoregulation after pediatric cardiac arrest," Resuscitation 85, pp. 1387-1393, Jun. 2014.
Lee, J. K. et al., "Cerebral blood flow and cerebrovascular autoregulation in a swine model of pediatric cardiac arrest and hypothermia*," Crit. Care Med. vol. 39, No. 10, pp. 2337-2345, Oct. 2011.
Lee, MD et al., "Cerebrovascular Reactivity Measured by Near-Infrared Spectroscopy," Stroke 40, pp. 1820-1826, Oct. 2009.
Lee, MD, et al., "Noninvasive autoregulation monitoring in a swine model of pediatric cardiac arrest," Anesth. Analg. vol. 114, pp. 825-836, Apr. 2012.
Lewis et al., "Continuous Correlation Between Intracranial Pressure and Cerebral Blood Flow Velocity Reflects Cerebral Autoregulation Impairment During Intracranial Pressure Plateau Waves," Neurocrit. Care 21, pp. 514-525, May 2014.
Liu et al., "Comparison of frequency and time domain methods of assessment of cerebral autoregulation in traumatic brain injury," J. Cereb. Blood Flow Metab. 35, pp. 248-256, Nov. 2014.
Nasr et al., "Baroreflex and Cerebral Autoregulation are Inversely Correlated," Circ. J. vol. 78, pp. 2460-2467, Oct. 2014.
Nasr et al., "Cerebral autoregulation in patients with obstructive sleep apnea syndrome during wakefulness," Eur. J. Neurol. 16, pp. 386-391, Mar. 2009.
Ono, MD et al., "Blood pressure excursions below the cerebral autoregulation threshold during cardiac surgery are associated with acute kidney injury," Crit. Care Med. 41, pp. 464-471, Feb. 2013.
Ono, MD et al., "Cerebral Blood Flow Autoregulation is Preserved After Hypothermic Circulatory Arrest," Ann. Thorac. Surg. 96, pp. 2045-2053, Dec. 2013.
Ono, MD et al., "Duration and magnitude of blood pressure below cerebral autoregulation threshold during cardiopulmonary bypass is associated with major morbidity and operative mortality," J. Thorac. Cardiovasc. Surg. 147, pp. 483-489, Jan. 2014.
Ono, MD et al., "Risks for impaired cerebral autoregulation during cardiopulmonary bypass and postoperative stroke," Br. J. Anaesth. 109, pp. 391-398, Jun. 2012.
Ono, MD et al., "Validation of a Stand-Alone Near-Infrared Spectroscopy System for Monitoring Cerebral Autoregulation During Cardiac Surgery," Anesth. Analg. vol. 116, No. 1, pp. 198-204, Jan. 2013.
Papademetriou et al., "Multichannel near infrared spectroscopy indicates regional variations in cerebral autoregulation in infants supported on extracorporeal membrane oxygenation," J. Biomed. Opt., vol. 17, pp. 067008-1-067008-9, Jun. 2012.

Radolovich et al., "Pulsatile Intracranial Pressure and Cerebral Autoregulation After Traumatic Brain Injury," Neurocrit. Care 15, pp. 379-386, Dec. 2011.
Radolovich et al., "Reactivity of Brain Tissue Oxygen to Change in Cerebral Perfusion Pressure in Head Injured Patients," Neurocrit. Care 10, pp. 274-279, Feb. 2009.
Reinhard, MD et al., "Cerebral Autoregulation in Carotid Artery Occlusive Disease Assessed From Spontaneous Blood Pressure Fluctuations by the Correlation Coefficient Index," Stroke 34, pp. 2138-2144, May 2003.
Reinhard, MD et al., "Cerebral dysautoregulation and the risk of ischemic events in occlusive carotid artery disease," J. Neurol. 255, pp. 1182-1189, Jun. 2008.
Schmidt et al., "Impaired autoregulation is associated with mortality in severe cerebral diseases" Clinical Neurosciences and Mental Health, 1 (Suppl. 1), May 2014, 6 pp.
Schmidt et al., "Asymmetry of cerebral autoregulation does not correspond to asymmetry of cerebrovascular pressure reactivity," Perspect. Med. 1-12, pp. 285-289, Sep. 2012.
Schmidt et al., "Cerebral Autoregulatory Response Depends on the Direction of Change in Perfusion Pressure," J. Neurotrauma 26, pp. 651-656, May 2009.
Severdija et al., "Assessment of dynamic cerebral autoregulation and cerebral carbon dioxide reactivity during normothermic cardiopulmonary bypass," Med. Biol. Eng. Comput. 53, pp. 195-203, Nov. 2014.
Smith, "Shedding light on the adult brain: a review of the clinical applications of near-infrared spectroscopy," Philos. Trans. R. Soc. A Math. Phys. Eng. Sci. 369, pp. 4452-4469 Oct. 2011.
Soul et al., "Fluctuating Pressure-Passivity is Common in the Cerebral Circulation of Sick Premature Infants," Pediatric Research 61, No. 4, Nov. 2007, pp. 467-473.
Steiner, MD et al., "Continuous monitoring of cerebrovascular pressure reactivity allows determination of optimal cerebral perfusion pressure in patients with traumatic brain injury," Crit. Care Med. 30, pp. 733-738, Apr. 2002.
Steiner et al., "Near-Infrared Spectroscopy Can Monitor Dynamic Cerebral Autoregulation in Adults," Neurocrit. Care 10, pp. 122-128, Sep. 2008.
Tekes et al., "Apparent Diffusion Coefficient Scalars Correlate with Near-Infrared Spectroscopy Markers of Cerebrovascular Autoregulation in Neonates Cooled for Perinatal Hypoxic-Ischemic Injury," Am. J. Neuroradiol. 36, pp. 188-193, Jan. 2015.
Zheng et al., "Continuous Cerebral Blood Flow Autoregulation Monitoring in Patients Undergoing Liver Transplantation," Neurocrit. Care 17, pp. 77-84, Aug. 2012.
Zweifel et al., "Continuous Assessment of Cerebral Autoregulation With Near-Infrared Spectroscopy in Adults After Subarachnoid Hemorrhage," Stroke 41, pp. 1963-1968, Jan. 2010.
Zweifel et al., "Continuous time-domain monitoring of cerebral autoregulation in neurocritical care," Med. Eng. Phys. 36, 638-645, Feb. 2014.
Tsalach et al., "Cerebral Autoregulation Real-Time Monitoring," PLOS One, Aug. 29, 2016, 14 pp.
Chung MD, PhD et al., "Assessment of Noninvasive Regional Brain Oximetry in Posterior Reversible Encephalopahty Syndrome and Reversible Cerebral Vasoconstriction Syndrome," Journal of Intensive Care Medicine, vol. 31(6), Jan. 2016, pp. 415-419.
Lee et al., "Cerebrovascular Autoregulation in pediatric moyamoya Disease" Pediatric Anesthesia, 23, pp. 547-556, Jun. 2013.
Steppan, MD, et al., "Cerebral and Tissue Oximetryc" Best Pract Res Clin Anaesthesiol, Dec. 2014, pp. 429-439.
Brady et al., "A New Monitor of Pressure Autoregulation: What Does It Add?" International Anesthesia Research Society, Nov. 2015, vol. 121, No. 5, pp. 1121-1123.
Prabhakar et al., "Current concepts of optimal cerebral perfusion pressure in traumatic brain injury," J. Anaesthesiol Clin Pharmacol, Jul.-Sep. 2014, pp. 318-327.
Lang et al., "Continuous monitoring of cerebrovascular autoregulation: a validation study," J Neurol Neurosurg Psychiatry, pp. 583-586, Jan. 2002.

(56) References Cited

OTHER PUBLICATIONS

Lazaridis et al., Optimal cerebral perfusion pressure: are we ready for it? Neurological Research, vol. 35, No. 2, Nov. 12, 2013, pp. 138-148.
Joshi et al., "Predicting the Limits of Cerebral Autoregulation During Cardiopulmonary Bypass," Anesthesia-Analgesia, Mar. 2012, vol. 114, No. 3, pp. 503-510.
Olsen et al., "Validation of Transcranial Near-Infrared Spectroscopy for Evaluation of Cerebral Blood Flow Autoregulation," Journal of Neurosurgical Anesthesiology, pp. 280-285, Oct. 1996.
Addison et al., "Gradient adjustment method for better discriminating correlating and non-correlating regions of physiological signals: application to the partitioning of impaired and intact zones of cerebral autoregulation," J Clin Moit Comput, Aug. 2016, 11 pp.
Montgomery et al., "Data clustering methods for the determination of cerebral autoregulation functionality," J Clin Monit Comput, Sep. 2015, 8 pp.
Brady et al., "The Lower Limit of Cerebral Blood Flow Autoregulation is Increased with Elevated Intracranial Pressure," vol. 108, No. 4, Apr. 2009.
Gao et al., "Mathematical considerations for modeling cerebral blood flow autoregulation to systemic arterial pressure," accessed on Sep. 19, 2016, accessed from http://ajpheart.physiology.org/., pp. H1023-H1031.
Hauerberg et al., "The Upper Limit of Cerebral Blood Flow Autoregulation in Acute Intracranial Hypertension," Journal of Neurosurgical Anesthesiology, vol. 10, No. 2, pp. 106-112, May 1998.
Hori et al., "Arterial pressure above the upper cerebral autoregulation limit during cardiopulmonary bypass is associated with post-operative delirium," British Journal of Anaesthesia Sep. 2014, pp. 1009-1017.
Kamar et al., "Detecting Cerebral Autoregulation Thresholds Using a Noninvasive Cerebral Flow Monitor," Ornim medical, May 2013, Portugal Poster, 1 pp.
Lucas et al., "Influence of Changes in Blood Pressure on cerebral Perfusion and Oxygenation," Hypertension, Oct. 2009, pp. 698-705.
Minassian et al., "Changes in intracranial pressure and cerebral autoregulation in patients with severe traumatic brain injury," vol. 30, Jul. 2002, pp. 1616-1622.
Pesek, MD, et al., "The upper limit of cerebral blood flow autoregulation is decreased with elevations in intracranial pressure," Neurosurgery, vol. 75, No. 2, Aug. 2014, pp. 163-170.
Sadoshima et al., "Upper Limit of Cerebral Autoregulation During Development of Hypertension in Spontaneously Hypertensive Rats—Effect of Sympathetic Denervation," vol. 16, No. 3, May-Jun. 1985, pp. 477-481.
Sadoshima et al., "Inhibition of Angiotensin-Converting Enzyme Modulates the Autoregulation of Regional Cerebral Blood Flow in Hypertensive Rats," vol. 23, No. 6, Part 1, Jun. 1994, pp. 781-785.
Strandgaard et al., "Upper Limit of Cerebral Blood Flow Autoregulation in Experimental Renovascular Hypertension in the Baboon," vol. 37, Aug. 1975, pp. 164-167.
Ragauskas et al., "Analysis of cerebrovascular autoregulation reactivity index electronic monitoring methods," vol. 114, No. 8, Jun. 2011, 6 pp.
Chiu et al., "Assessment of cerebral autoregulation using time-domain cross-correlation analysis," Computers Bio Med, Nov. 2001, pp. 471-480.
Larson et al., "Cerebrovascular autoregulation after rewarming from hypothermia in a neonatal swine model of asphyxic brain injury," J Appl Physiol. 115; pp. 1433-1442, Sep. 2013.
Petkus et al., "Novel Method and Device for Fully Non-Invasive Cerebrovascular Autoregulation Monitoring," Elektronika Ir Elektrotechnika, vol. 20, No. 8, pp. 24-29, Oct. 2014.
Olufsen et al., "Blood pressure and blood flow variation during postural change from sitting to standing: model development and validation," J Appl Physiol Oct. 2005, pp. 1523-1537.
Rangel-Castilla, MD, et al., "Cerebral pressure autoregulation in traumatic brain injury," Neurosurg Focus, vol. 25, Oct. 2008, 8 pp.
Addison, "A Review of Wavelet Transform Time-Frequency Methods for NIRS-Based Analysis of Cerebral Autoregulation," IEEE Reviews in Biomedical Engineering, vol. 8, 2015, pp. 78-85.
Moerman, M.D., Ph.D., et al., "Assessment of Cerebral Autoregulation Patterns with Near-infrared Spectroscopy during Pharmacological-induced Pressure Changes," Anesthesiology, vol. 123, No. 2, Aug. 2015, pp. 327-335.
U.S. Appl. No. 15/911,449, naming Paul S. Addison et al. as inventors, filed Mar. 5, 2018.
U.S. Appl. No. 15/962,438, naming Paul S. Addison et al. as inventors, filed Apr. 25, 2018.
U.S. Appl. No. 15/980,235, naming Paul S. Addison et al. as inventors, filed May 15, 2018.
U.S. Appl. No. 15/962,503, naming Paul S. Addison et al. as inventors, filed Apr. 25, 2018.
U.S. Appl. No. 15/962,468, naming Paul S. Addison et al. as inventors, filed Apr. 25, 2018.

\* cited by examiner

DETERMINING CHANGES TO AUTOREGULATION

TECHNICAL FIELD

This disclosure relates to physiological parameter monitoring.

BACKGROUND

Cerebral autoregulation (CA) is the response mechanism by which an organism regulates cerebral blood flow over a wide range of systemic blood pressure changes through complex myogenic, neurogenic, and metabolic mechanisms. Autoregulation dysfunction may result from a number of causes including, stroke, traumatic brain injury, brain lesions, brain asphyxia, or infections of the central nervous system. Intact cerebral autoregulation function occurs over a range of blood pressures defined between a lower limit of autoregulation (LLA) and an upper limit of autoregulation (ULA).

SUMMARY

This disclosure describes devices, systems, and techniques including processing circuitry configured to determine an estimate of a limit of autoregulation at least in part by determining that a physiological parameter is changing rapidly in a particular time period. In some examples, rapid changes in a physiological parameter indicate that the associated correlation coefficient values may be less accurate. Thus, to increase the accuracy of the correlation coefficient values and a resulting estimate of a limit of autoregulation, the processing circuitry is configured to select a correlation coefficient value associated with the particular time period and determine an updated value of the selected correlation coefficient value. The processing circuitry may use the updated value, along with a set of other correlation coefficient values, to determine an estimate of the limit of autoregulation and an autoregulation status of the patient.

Clause 1: In some examples, a device includes a display and processing circuitry configured to receive a first signal indicative of a first physiological parameter of a patient and a second signal indicative of a second physiological parameter of the patient. The processing circuitry is also configured to determine a set of correlation coefficient values for a set of values of the first physiological parameter and for a set of values of the second physiological parameter. The processing circuitry is further configured to determine that the first physiological parameter changes rapidly in a particular time period. The processing circuitry is configured to, in response to determining that the first physiological parameter changes rapidly in the particular time period, select a correlation coefficient value of the set of correlation coefficient values associated with the particular time period and determine an updated value of the selected correlation coefficient value. The processing circuitry is configured to determine an estimate of a limit of autoregulation of the patient based on set of the correlation coefficient values and the updated value of the selected correlation coefficient value. The processing circuitry is also configured to determine an autoregulation status of the patient based on the estimate of the limit of autoregulation and output, for display via the display, an indication of the autoregulation status.

Clause 2: In some examples of clause 1, the processing circuitry is configured to determine that the first physiological parameter changes rapidly in the particular time period at least in part by determining that a rate of change of the first physiological parameter in the particular time period exceeds a threshold rate.

Clause 3: In some examples of clause 2, the processing circuitry is further configured to dynamically determine the threshold rate based on previously determined values of the first physiological parameter.

Clause 4: In some examples of any of clauses 1-3, the processing circuitry is configured to determine that the first physiological parameter changes rapidly in the particular time period at least in part by determining that a rate of change of the correlation coefficient values in the particular time period exceeds a threshold rate.

Clause 5: In some examples of clause 4, the processing circuitry is further configured to dynamically determine the threshold rate based on previously determined correlation coefficient values.

Clause 6: In some examples of any of clauses 1-5, the processing circuitry is configured to determine that the first physiological parameter changes rapidly in the particular time period at least in part by determining that a product of the rate of change of the first physiological parameter and a rate of change of the correlation coefficient values in the particular time period exceeds a threshold rate.

Clause 7: In some examples of any of clauses 1-6, the processing circuitry is configured to determine the updated value of the selected correlation coefficient value at least in part by setting a value of the selected correlation coefficient value to one.

Clause 8: In some examples of any of clauses 1-7, the processing circuitry is configured to determine the estimate of the limit of autoregulation based on a window having a length of time, and the processing circuitry is further configured to shorten the length of time of the window in response to determining that the first physiological parameter changes rapidly in the particular time period.

Clause 9: In some examples of clause 8, the processing circuitry is further configured to determine a new length of time for the window based on a rate of change of the first physiological parameter in the particular time period.

Clause 10: In some examples of clause 8 or clause 9, the processing circuitry is further configured to determine a new length of time for the window based on a rate of change of correlation coefficient values in the particular time period.

Clause 11: In some examples of any of clauses 1-10, the processing circuitry is configured to determine updated values for the set of correlation coefficient values in response to determining that the first physiological parameter changes rapidly in the particular time period.

Clause 12: In some examples of any of clauses 1-11, the processing circuitry is configured to determine the set of correlation coefficient values during a window of time. The processing circuitry is configured to determine the estimate of the limit of autoregulation based on the set of correlation coefficient values during the window of time. The processing circuitry is configured to, after an end of the window of time, select the correlation coefficient associated with the particular time period and determine an updated value of the selected correlation coefficient.

Clause 13: In some examples of any of clauses 1-12, the processing circuitry is further configured to determine that a value of the first physiological parameter associated with the particular time period is less than a threshold value of the first physiological parameter. The processing circuitry is configured to determine the updated value of the selected correlation coefficient value in response to determining that the value of the first physiological parameter associated with the particular time period is less than the threshold value.

Clause 14: In some examples of any of clauses 1-13, the processing circuitry is configured to determine the estimate of the limit of autoregulation at least in part by determining an estimate of a lower limit of autoregulation. The processing circuitry is further configured to determine that a value of the first physiological parameter associated with the particular time period is less than the estimate of the lower limit of autoregulation. The processing circuitry is configured to determine the updated value of the selected correlation coefficient value in response to determining that the value of the first physiological parameter associated with the particular time period is less than the estimate of the lower limit of autoregulation.

Clause 15: In some examples, a method includes receiving, by processing circuitry of a device and from sensing circuitry of the device, a first signal indicative of a first physiological parameter of a patient and a second signal indicative of a second physiological parameter of the patient. The method also includes determining, by the processing circuitry, a set of correlation coefficient values for a set of values of the first physiological parameter and for a set of values of the second physiological parameter. The method further includes determining, by the processing circuitry, that the first physiological parameter changes rapidly in a particular time period. In response to determining that the first physiological parameter changes rapidly in particular time period, selecting, by the processing circuitry, a correlation coefficient value of the set of correlation coefficient values associated with the particular time period and determining, by the processing circuitry, an updated value of the selected correlation coefficient value. The method includes determining, by the processing circuitry, an estimate of a limit of autoregulation of the patient based on the set of correlation coefficient values and the updated value of the selected correlation coefficient value. The method also includes determining, by the processing circuitry, an autoregulation status of the patient based on the estimate of the limit of autoregulation and outputting, by the processing circuitry for display via the display, an indication of the autoregulation status.

Clause 16: In some examples of clause 15, determining that the first physiological parameter changes rapidly in the particular time period includes determining that a rate of change of the first physiological parameter in the particular time period exceeds a threshold rate.

Clause 17: In some examples of clause 15 or clause 16, determining that the first physiological parameter changes rapidly in the particular time period includes determining that a rate of change of the correlation coefficient values in the particular time period exceeds a threshold rate.

Clause 18: In some examples of any of clauses 15-17, determining that the first physiological parameter changes rapidly in the particular time period includes determining that a rate of change of the first physiological parameter in the particular time period exceeds a threshold rate.

Clause 19: In some examples, a device includes a display and processing circuitry configured to receive a first signal indicative of a first physiological parameter of a patient and a second signal indicative of a second physiological parameter of the patient. The processing circuitry is further configured to determine that the first physiological parameter changes rapidly. The processing circuitry is configured to, in response to determining that the first physiological parameter changes rapidly, shorten a length of time of a window in which to determine a set of correlation coefficient values for a set of values of the first physiological parameter and for a set of values of the second physiological parameter. The processing circuitry is configured to determine an estimate of a limit of autoregulation of the patient based on set of the correlation coefficient values. The processing circuitry is also configured to determine an autoregulation status of the patient based on the estimate of the limit of autoregulation and output, for display via the display, an indication of the autoregulation status.

Clause 20: In some examples of clause 19, the processing circuitry is further configured to determine a new length of time for the window based on at least one of a rate of change of the first physiological parameter or a rate of change of the correlation coefficient values.

Clause 21: In some examples, a device includes sensing circuitry configured to receive a first signal indicative of a first physiological parameter of a patient and a second signal indicative of a second physiological parameter of the patient. The device also includes processing circuitry configured to determine a set of correlation coefficient values for a set of values of the first physiological parameter and for a set of values of the second physiological parameter. The processing circuitry is further configured to determine that the first physiological parameter changes rapidly in a particular time period. The processing circuitry is configured to, in response to determining that the first physiological parameter changes rapidly in the particular time period, select a correlation coefficient value of the set of correlation coefficient values associated with the particular time period and determine an updated value of the selected correlation coefficient value. The processing circuitry is configured to determine an estimate of a limit of autoregulation of the patient based on set of the correlation coefficient values and the updated value of the selected correlation coefficient value. The processing circuitry is also configured to determine an autoregulation status of the patient based on the estimate of the limit of autoregulation and output, for display via a display, an indication of the autoregulation status.

The details of one or more examples are set forth in the accompanying drawings and the description below. Other features, objects, and advantages will be apparent from the description and drawings, and from the claims.

DETAILED DESCRIPTION

Figure 1:
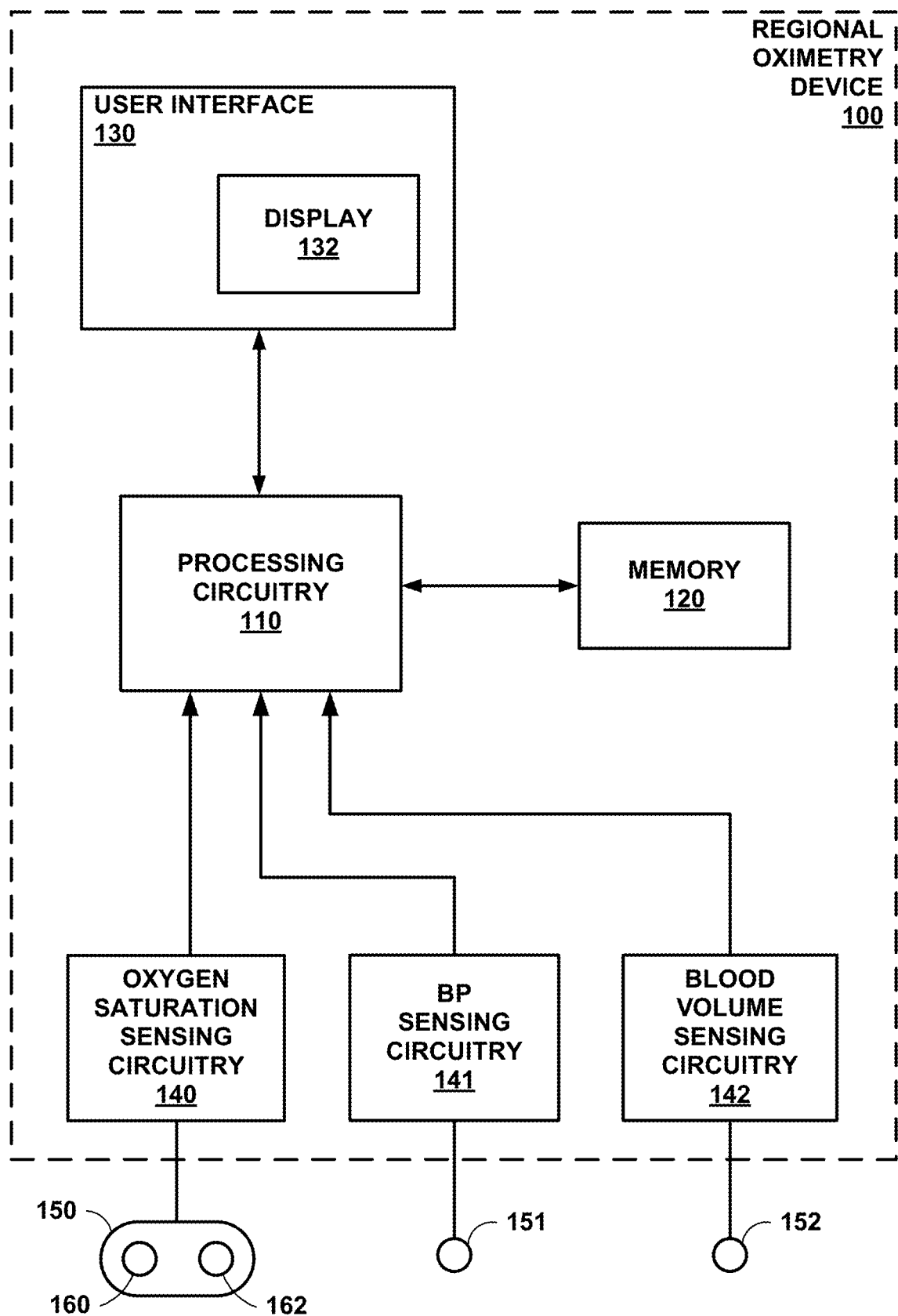
FIG. 1 is a conceptual block diagram illustrating an example regional oximetry device.

This disclosure describes devices, systems, and techniques for determining an estimate of a limit of autoregulation based on a set of correlation coefficient values. Processing circuitry of a regional oximetry device may determine the set of correlation coefficient values based on sets of values of two physiological parameters. The processing circuitry may determine an updated value (e.g., modify the value) of a selected correlation coefficient value associated with a rapid change in one of the physiological parameters. Accordingly, the processing circuitry may be able to determine a more accurate estimate of a limit of autoregulation, as compared to determining an estimate of the limit of autoregulation based on non-updated values of the correlation coefficient values.

The processing circuitry may be configured to determine that the first physiological parameter changes rapidly in the particular time period by using one or more of several techniques. As one example, the processing circuitry may be configured to determine that a rate of change of the first physiological parameter exceeds a first threshold rate. As another example, the processing circuitry may be configured to determine that a rate of change of the second physiological parameter exceeds a second threshold rate. As a further example, the processing circuitry may be configured to determine that a rate of change of the correlation coefficient values exceeds a third threshold rate. In another example, the processing circuitry may be configured to determine that a product of the rate of change of the first physiological parameter and a rate of change of the correlation coefficient values in the particular time period exceeds a fourth threshold rate. The examples described herein may be used in the alternative, or one or more of the techniques may be used together by the processing circuitry to identify rapid changes in the first physiological parameter. Other example techniques may additionally or alternatively be used.

The processing circuitry is configured to determine an updated value of the selected correlation coefficient value in response to determining that the first physiological parameter changes rapidly in the particular time period. By determining the updated value, the processing circuitry can cause the selected correlation coefficient value to have a reduced effect on the determination of an autoregulation status. The set of correlation coefficient values with the updated value(s) may be a more accurate representation of the patient state, as compared to a set of correlation coefficient values with value(s) that have not been updated.

A patient state, as indicated by sensed physiological signals, may change relatively rapidly over time. In response to a changing patient state, the values of a physiological parameter may change rapidly while the values of another physiological parameter may change less rapidly. Thus, the correlation coefficient values associated with time periods during and just after the change in patient state may not necessarily be an accurate reflection of the new patient state. Even if the patient state does not change, the values of a physiological parameter can change rapidly, and some or all of the rapidly changing values may not be accurate. Processing circuitry that determines updated values for correlation coefficient values associated with rapid changes in a physiological parameter can reduce the effect of selected correlation coefficient values that may be less likely to be accurate. Thus, the resulting estimate of a limit of autoregulation and determination of the patient's autoregulation status by the processing circuitry may be more accurate when the processing circuitry uses the updated value(s) of the selected correlation coefficient values.

The devices, systems, and techniques of this disclosure may allow for presenting a more accurate estimate of a limit of autoregulation of a patient and a more accurate indication of the autoregulation status of the patient. The presentation of more accurate and more stable information may result in increased confidence by a clinician viewing the presented information, which may lead to more informed decision making by the clinician. A clinician may lose confidence in the information presented by the processing circuitry if the information is less stable and/or less accurate. By determining updated values for correlation coefficient values associated with rapid changes, the processing circuitry may base the determination of autoregulation status on more stable values of physiological parameters. By determining an autoregulation status using the techniques of this disclosure, the processing circuitry may reduce swings in the estimates of limits of autoregulation caused by rapid changes in the physiological parameters.

The autoregulation status of a patient may be an indication that the cerebral autoregulation control mechanism of the patient is intact (e.g., functioning properly) or impaired (e.g., not functioning properly). A cerebral autoregulation control mechanism of the body may regulate cerebral blood flow (CBF) over a range of systemic blood pressures. This range of systemic blood pressures may lie within a lower limit of autoregulation (LLA) and an upper limit of autoregulation (ULA). Outside of the LLA and the ULA, blood pressure directly drives CBF, and cerebral autoregulation function may thus be considered impaired.

One method to determine the limits of autoregulation (e.g., the LLA and ULA) noninvasively using near-infrared spectroscopy (NIRS) technology may include the COx measure, which is a moving correlation index between mean arterial pressure (MAP) and regional oxygen saturation ($rSO_2$). The COx measure (e.g., the Pearson coefficient) is derived from the correlation between $rSO_2$ and MAP. COx relates to the regression line fit or linear correlation between $rSO_2$ and MAP over a time window having a particular length, such as three hundred seconds, in some examples. The COx method may be used to produce a representation of a patient's blood-pressure-dependent autoregulation status.

When the cerebral autoregulation is intact for a patient, there is typically no correlation between MAP and $rSO_2$. In contrast, MAP and $rSO_2$ typically directly correlate (e.g., the correlation index of COx is approximately 1) when the cerebral autoregulation is impaired. In practice, however, sensed data indicative of autoregulation may be noisy and/or there might be a slightly correlated relationship between variables (e.g., MAP and $rSO_2$) even when cerebral autoregulation is intact for the patient.

Some existing systems for monitoring autoregulation may determine a patient's autoregulation status based on various physiological parameter values (also referred to herein as physiological values). Such physiological values may be subject to various sources of error, such as noise caused by relative sensor and patient motion, operator error, poor quality measurements, drugs, or other anomalies. However, some existing systems for monitoring autoregulation may not reduce the various sources of error when utilizing the measured physiological values to determine the patient's autoregulation status. Furthermore, some existing systems may not determine and/or utilize a reliable metric to determine whether the autoregulation status calculated from the physiological values is reliable. Accordingly, the autoregulation status determined by such existing systems may be less accurate or less reliable.

In an intact region of cerebral autoregulation, there may be no correlation between these variables whereas in an impaired region of cerebral autoregulation, the correlation index should approximate unity. In practice, however, the data may be noisy and/or the intact region may exhibit a slightly positive relationship. This positive relationship may render traditional autoregulation limit calculations difficult to perform, resulting in the need for manual interpretation of the data using arbitrary thresholds. Further, the underlying mathematics of the technique may be asymmetric in terms of the results produced for impaired and intact regions and may be, in fact, not computable for the ideal case within the intact region.

A physician may monitor a patient's autoregulation through the use of various monitoring devices and systems that measure various physiological parameters. In certain aspects of the present disclosure, a patient's autoregulation may be monitored by correlating measurements of the patient's blood pressure (e.g., arterial blood pressure) with measurements of the patient's oxygen saturation (e.g., regional oxygen saturation). In particular, a cerebral oximetry index (COx) may be derived based at least in part on a linear correlation between the patient's blood pressure and oxygen saturation. In addition, in certain aspects of the present disclosure, the patient's autoregulation may be monitored by correlating measurements of the patient's blood pressure with measurements of the patient's blood volume (e.g., blood volume proxy). In particular, a hemoglobin volume index (HVx) may be derived based at least in part on a linear correlation between the patient's blood pressure and blood volume.

While features of the present disclosure are discussed with reference to COx, in other examples, various other linear correlations such as HVx may be determined to help evaluate a patient's autoregulation status. For example, a linear correlation between measurements of a patient's blood pressure and measurements of a patient's cerebral blood flow may derive a mean velocity index (Mx). As a further example, a linear correlation between measurements of a patient's blood pressure and measurements of a patient's intracranial pressure may derive a pressure reactivity index (PRx). In certain situations, these indexes may be utilized to determine or help evaluate a patient's autoregulation. The devices, systems, and techniques of this disclosure can also be applied to the determination of indices such as HVx, Mx, PRx, and/or any other indices, coefficients, and correlations. For example, processing circuitry may be configured to determine an estimate of a limit of autoregulation based on a set of HVx indices, a set of Mx indices, and/or a set of PRx indices.

Additional example details of the parameters that can be used for determining a limit of autoregulation may be found in commonly assigned U.S. Patent Application Publication No. 2016/0367197 filed on Jun. 16, 2016, entitled "Systems and Methods for Reducing Signal Noise When Monitoring Autoregulation," and commonly assigned U.S. Patent Application Publication No. 2017/0105631 filed on Oct. 18, 2016, entitled "System and Method for Providing Blood Pressure Safe Zone Indication During Autoregulation Monitoring," which are incorporated herein by reference in their entirety.

FIG. 1 is a conceptual block diagram illustrating an example regional oximetry device 100. Regional oximetry device 100 includes processing circuitry 110, memory 120, user interface 130, display 132, sensing circuitry 140-142, and sensing device(s) 150-152. In some examples, regional oximetry device 100 may be configured to determine and display the cerebral autoregulation status of a patient, e.g., during a medical procedure or for more long-term monitoring, such as fetal monitoring. A clinician may receive information regarding the cerebral autoregulation status of a patient via display 132 and adjust treatment or therapy to the patient based on the cerebral autoregulation status information.

Processing circuitry 110, as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of physiological parameters, MAP values, $rSO_2$ values, COx values, and value(s) of an LLA and/or a ULA, for example. Memory 120 may also be configured to store data such as updated correlation coefficient values, predetermined updated values, threshold rates, lengths of time windows, and/or estimates of limits of autoregulation. The updated correlation coefficient values, predetermined updated values, threshold rates, and/or lengths of time windows may stay constant throughout the use of device 100 and across multiple patients, or these values may change over time.

In some examples, memory 120 may store program instructions, which may include one or more program modules, which are executable by processing circuitry 110. When executed by processing circuitry 110, such program instructions may cause processing circuitry 110 to provide the functionality ascribed to it herein. The program instructions may be embodied in software, firmware, and/or RAMware. Memory 120 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a patient. For example, processing circuitry 110 may be configured to present blood pressure values, physiological parameter values, and indications of autoregulation status (e.g., cerebral autoregulation status) of a patient via display 132. In some examples, if processing circuitry 110 determines that the autoregulation status of the patient is impaired, then processing circuitry 110 may present a notification (e.g., an alert) indicating the impaired cerebral autoregulation status via display 132. As another example, processing circuitry 110 may present, via display 132, estimates of $rSO_2$ for a patient, an estimate of the blood oxygen saturation ($SpO_2$) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, a light emitting diode (LED) display, and/or any other suitable display. User interface 130 and/or display 132 may be part of a personal digital assistant, mobile phone, tablet computer, laptop computer, any other suitable computing device, or any combination thereof, with a built-in display or a separate display. User interface 130 may also include means for projecting audio to a user, such as speaker(s). Processing circuitry 110 may be configured to present, via user interface 130, a visual, audible, tactile, or somatosensory notification (e.g., an alarm signal) indicative of the patient's autoregulation status and/or a notification indicative of the patient's limit(s) of autoregulation.

User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection (e.g., communication interface 290 shown in FIG. 2).

Sensing circuitry 140-142 may be configured to receive physiological signals sensed by respective sensing device(s) 150-152 and communicate the physiological signals to processing circuitry 110. Sensing device(s) 150-152 may include any sensing hardware configured to sense a physiological parameter of a patient, such as, but not limited to, one or more electrodes, optical receivers, blood pressure cuffs, or the like. Sensing circuitry 140-142 may convert the physiological signals to usable signals for processing circuitry 110, such that processing circuitry 110 is configured to receive signals generated by sensing circuitry 140-142. Sensing circuitry 140-142 may receive signals indicating physiological parameters from a patient, such as, but not limited to, blood pressure, regional oxygen saturation, blood volume, heart rate, and respiration. Sensing circuitry 140-142 may include, but are not limited to, blood pressure sensing circuitry, oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140-142 and/or processing circuitry 110 may include signal processing circuitry such as an analog-to-digital converter.

In some examples, oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

In such cases, oxygen saturation sensing device 150 may include emitter 160 and detector 162. Emitter 160 may include at least two light emitting diodes (LEDs), each configured to emit at different wavelengths of light, e.g., red or near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160. Light intensity of multiple wavelengths may be received at both the "close" and the "far" detector 162. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 150 may provide the regional oxygen saturation signal to processing circuitry 110 or to any other suitable processing device to enable evaluation of the patient's autoregulation status.

In operation, blood pressure sensing device 151 and oxygen saturation sensing device 150 may each be placed on the same or different parts of the patient's body. For example, blood pressure sensing device 151 and oxygen saturation sensing device 150 may be physically separate from each other and may be separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation. One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). For example, blood pressure sensing device 151 may include a blood pressure cuff for non-invasively monitoring blood pressure or an arterial line for invasively monitoring blood pressure. In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor.

Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring," the entire content of which is incorporated herein by reference. In other cases, the patient's blood pressure may be continuously, non-invasively monitored via multiple pulse oximetry sensors placed at multiple locations on the patient's body. As described in commonly assigned U.S. Pat. No. 6,599,251, entitled "Continuous Non-invasive Blood Pressure Monitoring Method and Apparatus," the entire content of which is incorporated herein by reference, multiple PPG signals may be obtained from the multiple pulse oximetry sensors, and the PPG signals may be compared against one another to estimate the patient's blood pressure. Regardless of its form, blood pressure sensing device 151 may be configured to generate a blood pressure signal indicative of the patient's blood pressure (e.g., arterial blood pressure) over time. Blood pressure sensing device 151 may provide the blood pressure signal to sensing circuitry 141, processing circuitry 110, or to any other suitable processing device to enable evaluation of the patient's autoregulation status.

Processing circuitry 110 may be configured to receive one or more signals generated by sensing devices 150-152 and sensing circuitry 140-142. The physiological signals may include a signal indicating blood pressure, a signal indicating oxygen saturation, and/or a signal indicating blood volume of a patient (e.g., an isosbestic signal). Processing circuitry 110 may be configured to determine a set of values of a first physiological parameter and a set of values of a second physiological parameter based on two or more signals received by sensing devices 150-152 and sensing circuitry 140-142 and delivered to processing circuitry 110. Sensing devices 150-152 and sensing circuitry 140-142 can deliver the physiological signals directly to processing circuitry 110 or sensing circuitry 140-142 can modify the physiological signals (e.g., through pre-processing) before delivering signals to processing circuitry 110. The first and second physiological parameters may include mean arterial pressure, oxygen saturation, and/or blood volume. Processing circuitry 110 may associate each value in a set of values with a point in time. For example, processing circuitry 110 may determine a value of mean arterial pressure at a particular time based on the characteristics of a blood pressure signal over a time interval.

Processing circuitry 110 may be configured to determine a set of correlation coefficient values for the set of values of the first physiological parameter and for the set of values of the second physiological parameter. Processing circuitry 110 may determine each correlation coefficient value for a sample of the values of the first physiological parameter and for a sample of the values of the second physiological parameter. For example, processing circuitry 110 may determine each correlation coefficient value based on a Pearson coefficient that measures the strength and direction of a linear relationship between the values of the first physiological parameter and for a sample of the values of the second physiological parameter.

Processing circuitry 110 may use a sampling window of, e.g., five or ten seconds for the values of each physiological parameter to determine each correlation coefficient value. Processing circuitry 110 may associate the correlation coefficient value with an average value of a first physiological parameter across the sampling window. The graphs of FIGS. 4-7B plot correlation coefficient values along a vertical axis and the associated values of the first physiological parameter along a horizontal axis. The correlation coefficient values (e.g., COx values or HVx values) may range from negative one to positive one. Processing circuitry 110 may also associate each value of a physiological parameter and each correlation coefficient value with a particular time period, as shown in indicators 310, 320, and 330 of FIG. 3.

Processing circuitry 110 is configured to determine whether the first physiological parameter changes rapidly in a particular time period. Processing circuitry 110 can determine a rapid change in the first physiological parameter at least in part by determining the rate of change of a physiological parameter, such as MAP, rSO$_2$, or blood volume under sensor (BVS), exceeds a threshold rate. Processing circuitry 110 may determine the rate of change of the MAP values as shown in Equation (1).

$$\text{Rate of change of } MAP \text{ values} = \frac{MAP_{i+k} - MAP_i}{\text{time}_{i+k} - \text{time}_i} \quad (1)$$

Processing circuitry 110 can use consecutive or non-consecutive MAP values to determining the rate of change of the MAP values. For consecutive values, k equals one, and for non-consecutive values, k equals an integer greater than one. Processing circuitry 110 may be configured to determine whether the rate of change of MAP values exceeds a threshold rate in a particular time period. The threshold rate for MAP values may be, for example, one, two, three, or four mmHg per second or any other suitable threshold rate.

Processing circuitry 110 can determine a rapid change in the first physiological parameter at least in part by determining the rate of change of the correlation coefficient values exceeds a threshold rate. Processing circuitry 110 may determine the rate of change of the correlation coefficient values as shown in Equation (2).

$$\text{Rate of change of } COx = \frac{COx_{i+k} - COx_i}{\text{time}_{i+k} - \text{time}_i} \quad (2)$$

Processing circuitry 110 can use consecutive or non-consecutive correlation coefficient values to determining the rate of change of the correlation coefficient values. For consecutive values, k equals one, and for non-consecutive values, k equals an integer greater than one. Processing circuitry 110 may be configured to determine whether the rate of change of correlation coefficient values exceeds a threshold rate in a particular time period. The threshold rate for correlation coefficient values may be, for example, 0.1, 0.2, 0.3, or 0.4 per second or any other suitable threshold rate.

In response to determining that the first physiological parameter changes rapidly in a particular time period, processing circuitry 110 is configured to select a correlation coefficient value associated with the particular time period and determine an updated value for the selected correlation coefficient value. For example, if processing circuitry 110 uses Equation (1) to determine that the rate of change of the MAP values exceeds a threshold rate, processing circuitry 110 may select the correlation coefficient value associated with a particular time period including all or part of the time period from time$_i$ to time$_{i+k}$. For example, processing circuitry 110 may determine an updated value of the selected correlation coefficient value at least in part by setting the selected correlation coefficient value to a predetermined updated value, such as positive one (unity), zero, negative one, +0.5, −0.5, or any other suitable value. In some examples, processing circuitry 110 marks the selected correlation coefficient value as invalid, e.g., discards the selected correlation coefficient value from consideration in the window of time.

Processing circuitry 110 is also configured to determine an estimate of a limit of autoregulation of a patient based on the set of correlation coefficient values and the updated value of the selected correlation coefficient value. The correlation coefficient values may be near positive one at very low values and very high values of the first physiological parameter (see, e.g., FIGS. 4-7B). Therefore, to determine an estimate of the lower limit of autoregulation, processing circuitry 110 may determine the lowest value of the first physiological parameter at which the associated correlation coefficient values are below a threshold level, such as 0.8, 0.7, 0.6, 0.5, 0.4, 0.3, 0.2, 0.1, or 0.0. To determine an estimate of the upper limit of autoregulation, processing circuitry 110 may determine the highest value of the first physiological parameter at which the associated correlation coefficient values are below a threshold level.

Processing circuitry 110 is also configured to determine an autoregulation status of the patient based on the estimate of the limit of autoregulation. For example, processing circuitry 110 may determine whether the current MAP value of the patient is greater than the estimate of the lower limit of autoregulation. If the current MAP value is greater than the estimate of the lower limit of autoregulation, then processing circuitry 110 can determine that the patient has intact autoregulation, unless the current MAP value is greater than the upper limit of autoregulation of the patient.

Processing circuitry 110 is configured to output, for display via display 132 of user interface 130, an indication of the autoregulation status. To present an indication of autoregulation status, display 132 may present a graphical user interface such as graphical user interface 300 shown in FIG. 3. As described in further detail below, graphical user interface 300 includes an indicator of autoregulation status 350. The indication of autoregulation status may include text, colors, and/or audio presented to a user. Processing circuitry 110 may be further configured to present an indication of one or more limits of autoregulation (e.g., indicators 360 and 370).

By determining that a physiological parameter changes rapidly, processing circuitry 110 may identify a particular time period that is more likely to be associated with inaccurate data. For example, a first physiological parameter may change rapidly while a second physiological parameter may change more slowly. Thus, the correlation coefficient values during a particular time period associated with a rapid change may not necessarily be accurate because the physiological parameters may be changing at different rates. The values of the slower-changing physiological parameter may not accurately indicate a recent change in the patient state, or the value of the faster-changing physiological parameter may overshoot the actual change in the patient state. The inaccurate values of a physiological parameter may cause processing circuitry 110 to determine correlation coefficient values that do not accurately reflect the patient state.

Processing circuitry 110 may be configured to determine an estimate of a limit of autoregulation based on correlation coefficient values across a time window. Processing circuitry 110 can use a time window with a length of two hundred seconds, three hundred seconds, four hundred seconds, or any other suitable length of time. Processing circuitry 110 may be configured to shorten the length of time of the time window in response to determining that a physiological parameter changes rapidly, thereby removing the least recent data from the determination of autoregulation status. By shortening the length of the time window, processing circuitry 110 may reduce the effect of correlation coefficient values associated with the times at the beginning of the time window (e.g., before the change in patient state). Shortening the length of the time window may effectively increase the weighting of the more recent correlation coefficient values.

In some examples, processing circuitry 110 may be configured to determine a new length of time for the window based on the rate of change of the first physiological parameter and/or the rate of change of the correlation coefficient values, and use the new window length going forward or for a predefined time period after the determination. Processing circuitry 110 can determine a shorter length of time for more rapid changes and a longer length of time for less rapid changes. Thus, in some examples the shortening of the window may be function of the rapidity or gradient of the MAP change and/or the correlation coefficient values change.

Although other example devices, systems, and techniques are possible, regional oximetry device 100 may be configured to determine the first estimate of the limit of autoregulation based on COx values derived from MAP values and $rSO_2$ values. Alternatively, processing circuitry 110 may determine the first estimate of the limit of autoregulation based on HVx values, BVS values, and/or $rSO_2$ values. Regional oximetry device 200 of FIG. 2 includes additional detail on how processing circuitry 110 can determine $rSO_2$ values based on a physiological signal received from sensing device 150.

Figure 2:
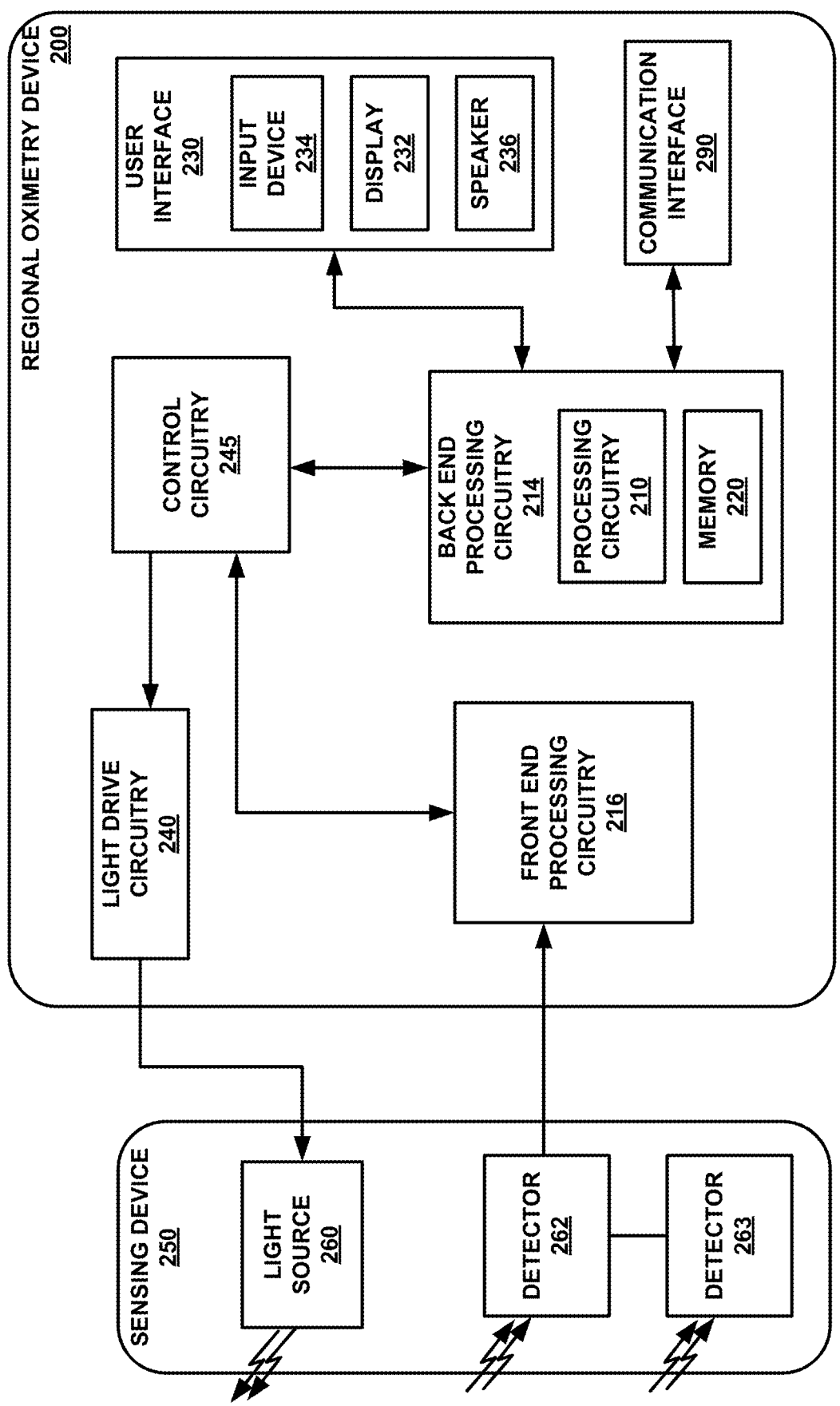
FIG. 2 is a conceptual block diagram illustrating an example regional oximetry device for monitoring the autoregulation status of a patient.

FIG. 2 is a conceptual block diagram illustrating an example regional oximetry device 200 for monitoring the autoregulation status of a patient. In the example shown in FIG. 2, regional oximetry device 200 is coupled to sensing device 250 and may be collectively referred to as a regional oximetry system, which each generate and process physiological signals of a subject. In some examples, sensing device 250 and regional oximetry device 200 may be part of an oximeter. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of regional oximetry device 100 shown in FIG. 1. In some examples, regional oximetry device 200 may also include a blood pressure sensor and/or a blood volume sensor (e.g., sensing devices 151 and 152 shown in FIG. 1).

In the example shown in FIG. 2, sensing device 250 includes light source 260, detector 262, and detector 263. In some examples, sensing device 250 may include more than two detectors. Light source 260 may be configured to emit photonic signals having two or more wavelengths of light (e.g., red and infrared (IR)) into a subject's tissue. For example, light source 260 may include a red light emitting light source and an IR light emitting light source, (e.g., red and IR light emitting diodes (LEDs)), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

In some examples, detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

After converting the received light to an electrical signal, detectors 262 and 263 may send the detection signals to regional oximetry device 200, where the detection signals may be processed and physiological parameters may be determined (e.g., based on the absorption of the red and IR wavelengths in the subject's tissue at both detectors). In some examples, one or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110. Processing circuitry 210 may receive and further process physiological signals received from front-end processing circuitry 216. For example, processing circuitry 210 may determine one or more physiological parameter values based on the received physiological signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, processing circuitry 210 is configured to receive signals indicative of physiological parameters. Processing circuitry 210 is also configured to determine values of physiological parameters based on the signals and determine correlation coefficient values based on the values of the physiological parameters. Processing circuitry 210 may be configured to select a correlation coefficient value associated with a rapid change in correlation coefficient values and determine an updated value for the selected correlation coefficient values. Processing circuitry 210 is also configured to determine a limit of autoregulation based on a set of correlation coefficient values including the updated value of the selected correlation coefficient value.

Memory 220 may include any suitable computer-readable media capable of storing information that can be interpreted by processing circuitry 210. In some examples, memory 220 may store correlation coefficient values, threshold rates, threshold values, window lengths, reference absorption curves, reference sets, determined values, such as blood oxygen saturation, pulse rate, blood pressure, fiducial point locations or characteristics, initialization parameters, any other determined values, or any combination thereof, in a memory device for later retrieval. Back-end processing circuitry 214 may be communicatively coupled with user interface 230 and communication interface 290.

User interface 230 may include input device 234, display 232, and speaker 236. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include any type of user input device such as a keyboard, a mouse, a touch screen, buttons, switches, a microphone, a joy stick, a touch pad, or any other suitable input device or combination of input devices. In other examples, input device 234 may be a pressure-sensitive or presence-sensitive display that is included as part of display 232. Input device 234 may also receive inputs to select a model number of sensing device 250, blood pressure sensor 250 (FIG. 2), or blood pressure processing equipment. In some examples, processing circuitry 210 may determine a threshold rate and/or a length of a window of time based on user input received from input device 234.

Figure 3:
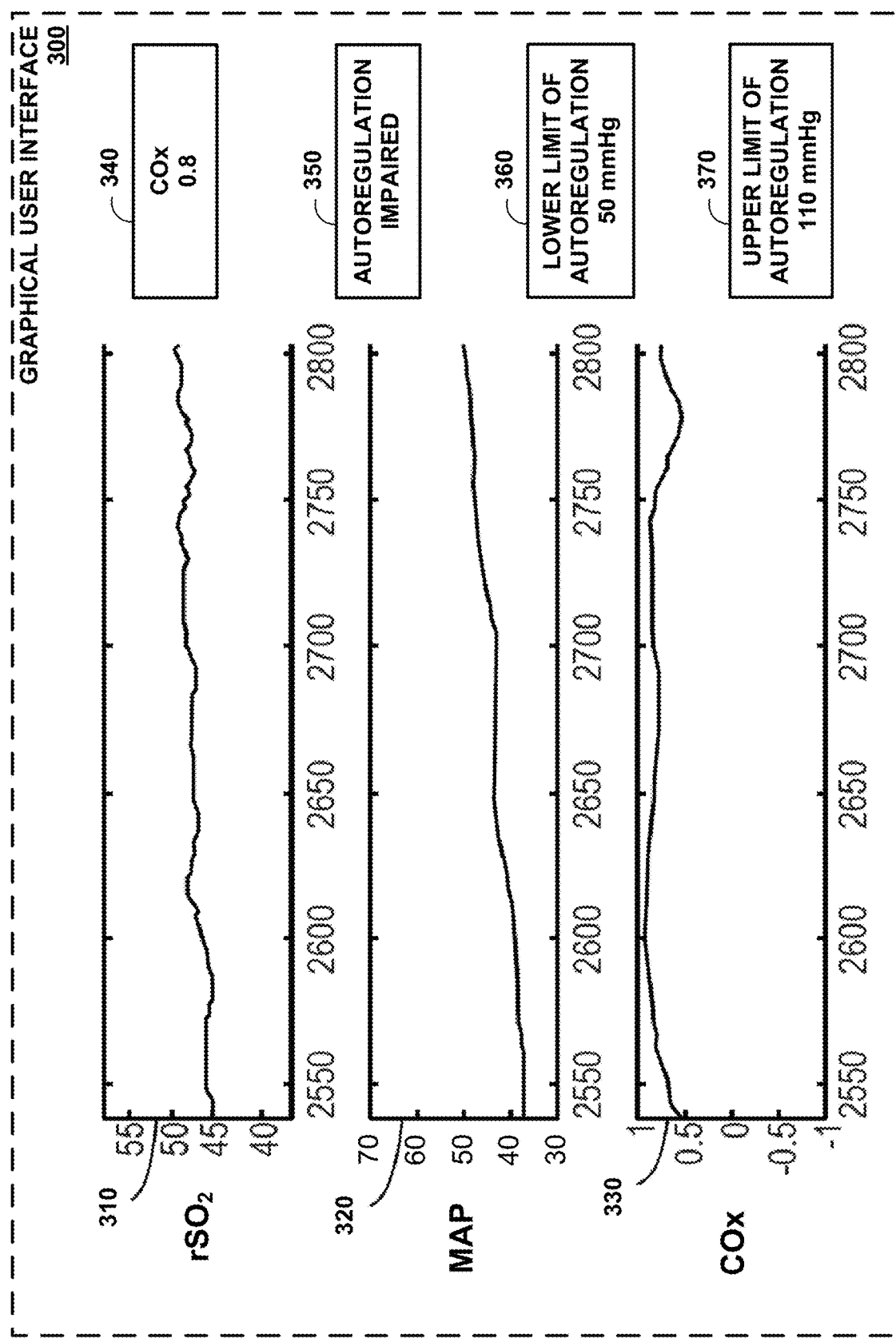
FIG. 3 illustrates an example graphical user interface including autoregulation information presented on a display.

In some examples, the subject may be a medical patient and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2. Additionally, display 232 may present, for example, one or more estimates of a subject's regional oxygen saturation generated by regional oximetry device 200 (referred to as an "rSO$_2$" measurement). Display 232 may also present indications of the upper and lower limits of autoregulation. Speaker 236 within user interface 230 may provide an audible sound that may be used in various examples, such as for example, sounding an audible alarm in the event that a patient's physiological parameters are not within a predefined normal range.

Communication interface 290 may enable regional oximetry device 200 to exchange information with external devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front-end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front-end processing circuitry 216, in back-end processing circuitry 214, or both. In other examples, the functionality of one or more of the components may be performed in a different order or may not be required. In some examples, all of the components of regional oximetry device 200 can be realized in processor circuitry.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Graphical user interface 300 may be configured to display various information related to blood pressure, oxygen saturation, the COx index, limits of autoregulation, and/or autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of regional oximetry device 100. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO$_2$ values and COx values, respectively, as discrete points, in a table, as a moving average, as a waveform, and/or as a single value.

COx signal indicator 330 may present a set of correlation coefficient values determined by processing circuitry 110. Processing circuitry 110 may determine the correlation coefficient values as a function of the oxygen saturation values presented in oxygen saturation signal indicator 310 and the MAP values presented in blood pressure signal indicator 320. In some examples, a COx value at or near one indicates the autoregulation status of a patient is impaired, as shown in autoregulation status indicator 350.

Processing circuitry 110 may determine a set of correlation coefficient values and associated values of a first physiological parameter using the values presented in indicators 310, 320, and/or 330. Processing circuitry 110 may determine a particular time period in indicators 310 or 320 during which a value of rSO$_2$ changes rapidly, a value of MAP changes rapidly, or a product of rSO$_2$ and MAP changes rapidly. Processing circuitry 110 may be configured to select a COx value associated with the particular time period from the COx values shown in indicator 330. Processing circuitry 110 then determines an updated value for the selected COx value in response to determining that a value of rSO$_2$ changes rapidly, a value of MAP changes rapidly, or a product of rSO$_2$ and MAP changes rapidly.

Processing circuitry 110 may be configured to determine an estimate of a limit of autoregulation based on correlation coefficient values across a time window for data collection. For example, the length of the time window may be two hundred seconds. At time 2750 (seconds) shown in indicators 310, 320, and 330, processing circuitry 110 may determine a rapid change in the MAP values. Processing circuitry 110 may be configured to shorten the length of the time window to a predefined shorter time window in response to determining a rapid change in the MAP values. The shortened length can be 250 seconds, 200 seconds, 150 seconds, 100 seconds, 50 seconds, and/or any other suitable length of time. Processing circuitry 110 may be configured to indefinitely use the shortened length for the window or revert to the original length after a predefined time period, such as thirty seconds or sixty seconds. In some examples, processing circuitry 110 may revert to the original window length in response to determining that the MAP values, rSO$_2$ values, and/or COx values are no longer changing rapidly. In some examples, processing circuitry 110 is configured to determine a new length for the time window based on a rate of change of the rSO$_2$ values and/or a rate of change of the MAP values. By shortening the time window for determining autoregulation status, processing circuitry 110 may increase the effect of recent correlation coefficient values on the determination of the estimate of a limit of autoregulation.

COx value indicator 340 shows a COx value of 0.8, which may result in a determination by processing circuitry 110 that the autoregulation status of the patient is impaired. Processing circuitry 110 may be configured to present, as the COx value in COx value indicator 340, the most recently determined COx value or a moving average of recently determined COx values. To determine the autoregulation status of a patient for presentation in autoregulation status indicator 350, processing circuitry 110 may determine whether the most recent MAP value shown in blood pressure signal indicator 320 is between the limits of autoregulation presented in limit of autoregulation indicators 360 and 370.

Processing circuitry 110 may present limit of autoregulation indicators 360 and/or 370 in terms of blood pressure, for example, mmHg. Processing circuitry 110 can determine the limits of cerebral autoregulation (LLA and ULA) for presentation in indicators 360 and 370 based on a relationship between the blood pressure of a patient and another physiological parameter of the patient. For example, indicator 350 and/or indicator 360 may be highlighted when the LLA has been exceeded or indicator 360 may be highlighted when the ULA has been exceeded. In other examples, a single indicator may present the type of limit that has been exceed by the MAP value. If the LLA or ULA change, processing circuitry 110 may control user interface 300 to change the value of the LLA or ULA in accordance with any change to that respective value.

Processing circuitry 110 may determine an estimate of a lower limit of autoregulation presented in indicator 360 and/or an estimate of an upper limit of autoregulation presented in indicator 370. Processing circuitry 110 may determine the estimates based on a set of correlation coefficient values including one or more updated values. Processing circuitry 110 may be configured to generate a notification in response to determining that the MAP value is less than or equal to the estimate of the lower limit of autoregulation. Processing circuitry 110 may output the notification in autoregulation status indicator 350 as text, color, blinking, and/or any other suitable visible or audible manner.

Figure 4:
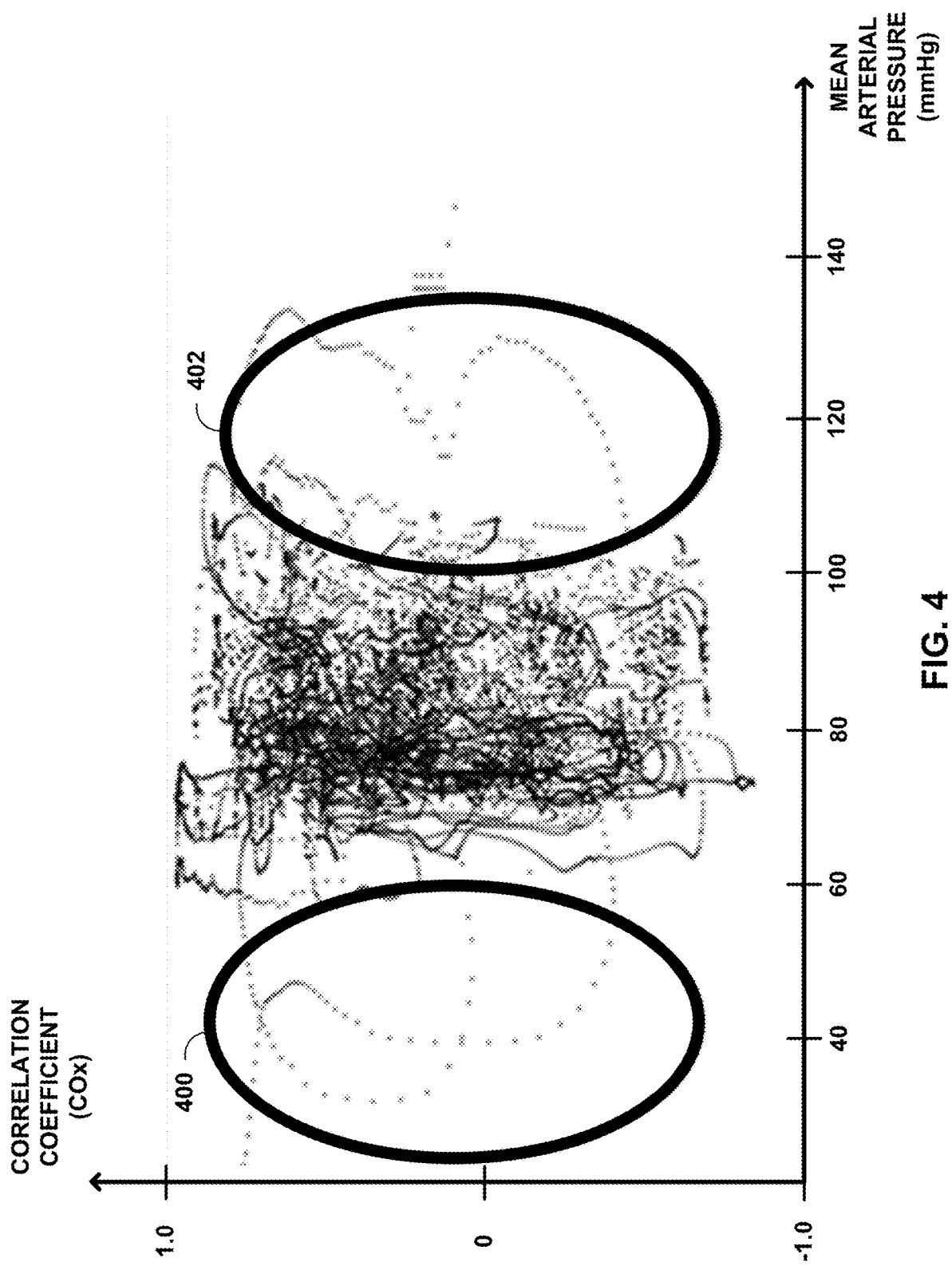
FIG. 4 is an example graph showing anomalous cerebral oximetry index (COx) values at high values and low values of mean arterial pressure.

FIG. 4 is an example graph showing anomalous COx values at high values and low values of mean arterial pressure. The graph of FIG. 4 plots COx values along the vertical axis and plots the MAP value associated with each correlation coefficient value along the horizontal axis. Some of the COx values in sections 400 and 402 are associated with rapidly changing MAP values, rapidly changing rSO$_2$ values, and/or rapidly changing COx values. The graph of FIG. 4 depicts rapid changes in MAP values between two consecutive data points by showing horizontal distance between the two data points. The graph of FIG. 4 depicts rapid changes in COx values between consecutive data points by showing vertical distance between data points.

Some or all of the COx values in section 400 are associated with MAP values that are less than the lower limit of autoregulation, which may be approximately sixty mmHg in the example of FIG. 4. Some or all of the COx values in section 402 are associated with MAP values that are greater than the upper limit of autoregulation, which may be approximately 100 or 110 mmHg in the example of FIG. 4. Thus, processing circuitry 110 can select those COx values identified as likely associated with rapid changes in MAP values, rapid changes in rSO$_2$ values, and/or rapid changes in COx values. Processing circuitry 110 may be configured to determine updated values for the selected COx values. Applying this type of correction may help ensure that COx values in the impaired regions are not artificially low due to a 300-second window length.

In some examples, processing circuitry 110 is configured to select correlation coefficient values that are associated with values of the first physiological parameter less than a threshold value. Processing circuitry 110 may set the threshold value depending on the current MAP value and the current assessment of the autoregulation state by setting the threshold value based on an estimate of the lower limit of autoregulation. In some examples, processing circuitry 110 is configured to set the threshold value equal to the estimate of the limit of autoregulation. For example, in response to determining a lower limit of autoregulation of 50 mmHg, processing circuitry 110 may set the threshold value for correcting a large change at or below 50 mmHg, such as 40 or 45 mmHg. By setting a threshold value, processing circuitry 110 may select and determine updated values for only the rapidly changing correlation coefficient values at the very low MAP values.

There are several scenarios in which rapid changes in a first physiological parameter may cause processing circuitry 110 to determine anomalous COx values due to a long correlation window length, such as three hundred seconds. For example, at a low COx value (e.g., in an intact region of autoregulation), the blood pressure of the patient may increase or decrease rapidly, causing the blood pressure to enter an impaired region of autoregulation. Due to the long window length, the COx values may only gradually increase to positive one in response to the blood pressure change. Thus, the change in the COx values will not match the speed of the rapid change in blood pressure. The slow increase in COx values means that the COx values in the impaired region will be lower than expected for a stable blood pressure, which may confound the accurate determination of autoregulation. This situation may be compounded by the relatively small number of data points in the impaired regions. Hence the anomalous values may disproportionately affect data at blood pressures less than the lower limit of autoregulation and at blood pressures greater than upper limit of autoregulation.

Figure 5:
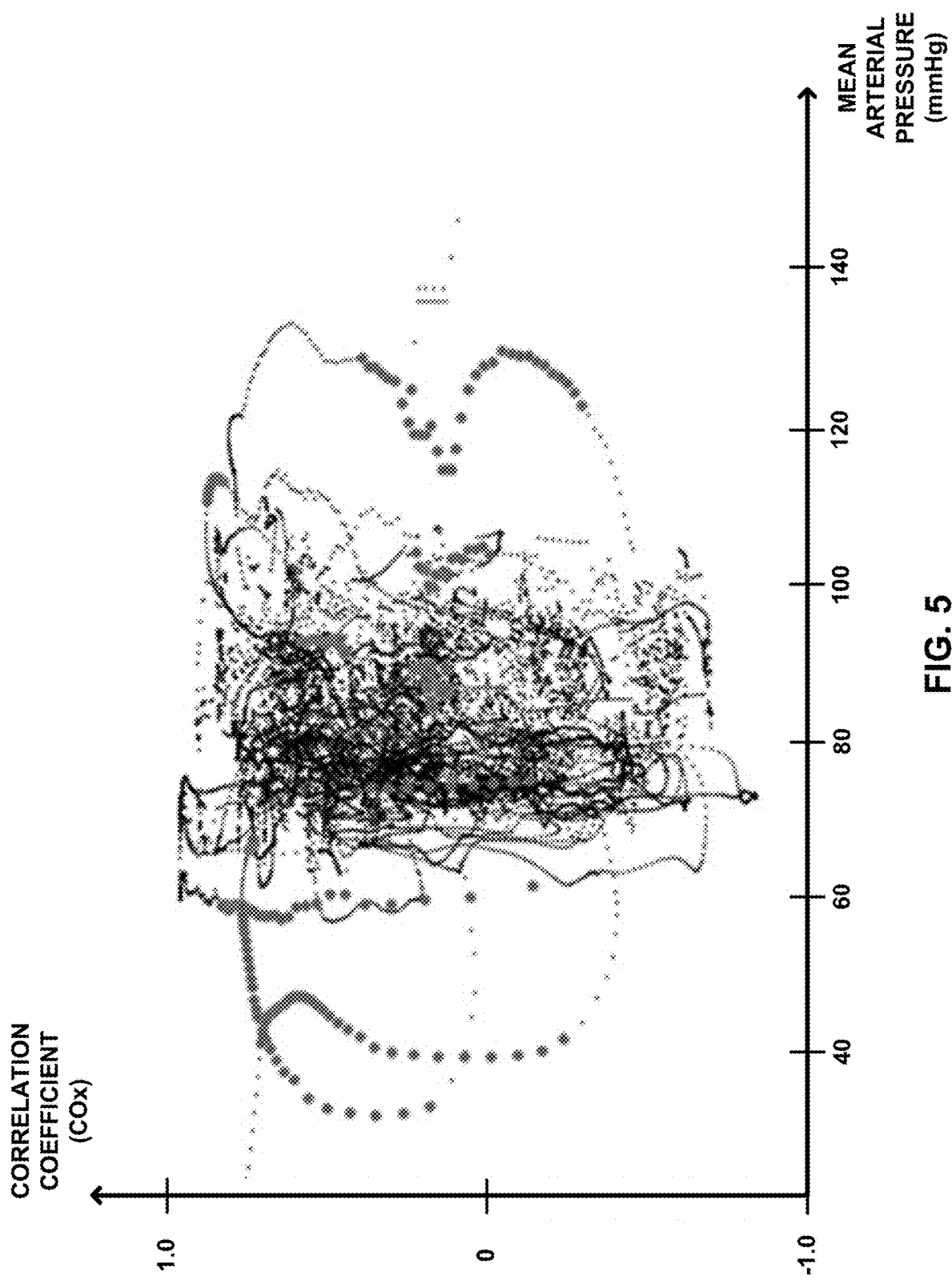
FIG. 5 is a graph illustrating the example graph of FIG. 4 modified to show the anomalous COx values as large grey circles.

FIG. 5 is a graph illustrating the example graph of FIG. 4 modified to show the suspected anomalous COx values as large grey circles. The anomalous COx values shown as large grey circles are examples of "selected correlation coefficient values" that are selected by processing circuitry 110. Processing circuitry 110 may determine which COx values are potentially anomalous by selecting the COx values associated with rapid changes in MAP values, rapid changes in $rSO_2$ values, and/or rapid changes in COx values, in some examples. The grey circles shown in the graph of FIG. 5 indicate the COx values associated with rapidly changing values.

Some of the selected COx values are plotted near the intact area of autoregulation (e.g., centered about eighty mmHg), while other selected COx values are plotted at the extreme MAP values in the graph of FIG. 5. Given the large number of COx values plotted near eighty mmHg, processing circuitry 110 will not significantly affect the determination of a limit of autoregulation by setting updated values for the selected COx values plotted near eighty mmHg. However, processing circuitry 110 can affect the determined limit of autoregulation by setting updated values for the selected COx values plotted at very low MAP values and very high MAP values.

Correcting the selected correlation coefficient values can also result in a number of COx values in the intact region being set to positive one. The sensitivity (to impaired regions) increases with a trade-off in decreased specificity. This decrease is not likely to significantly affect the determination of autoregulation status because there should be a large number of data points in the intact region (e.g., around eighty mmHg). The techniques of this disclosure may avoid the possibility of reporting an intact state when the state is in fact impaired, while having a much smaller possibility of reporting an impaired state when the state is actually intact.

Figure 6:
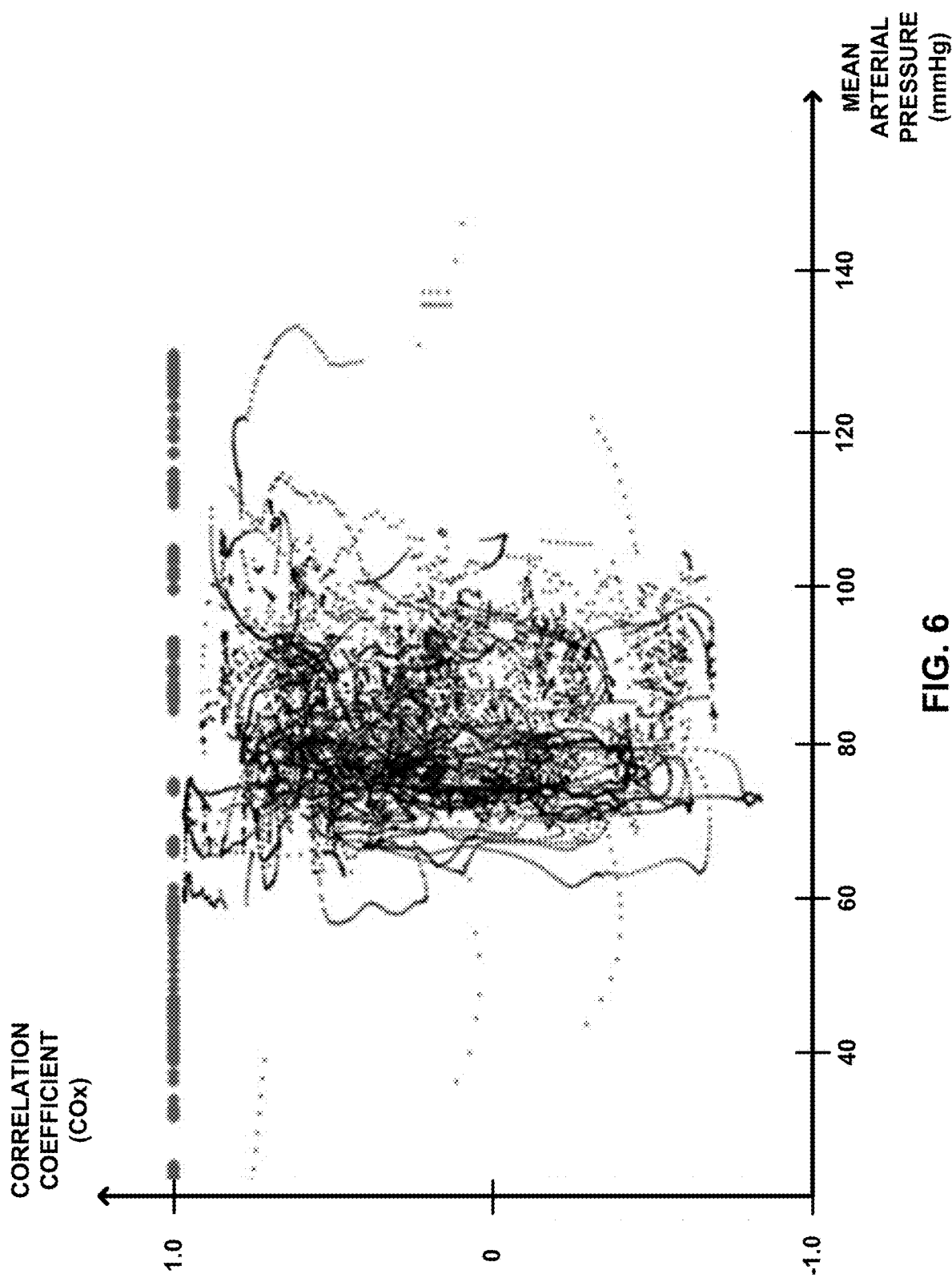
FIG. 6 is a graph illustrating the example graphs of FIGS. 4 and 5 modified to show the anomalous COx values as large grey circles after adjustment.

FIG. 6 is a graph illustrating the example graphs of FIGS. 4 and 5 modified to show the anomalous COx values as large grey circles after adjustment. The graph of FIG. 6 illustrates the corrected COx plot where processing circuitry 110 has moved the erroneous data marked in FIGS. 4 and 5 to new locations with COx values of positive one (unity). In the example of FIG. 6, processing circuitry 110 has determined an updated value of the selected COx values by setting the selected COx values to positive one. Setting the selected COx values to positive one may effectively reduce the effect of the selected COx values on the determination of the limits of autoregulation, especially if processing circuitry 110 determines an estimate of a limit of autoregulation based on a threshold COx level. If processing circuitry 110 determines an estimate of the lower limit of autoregulation in response to determining the lowest bin of COx values at which the mean COx value is less than a threshold value, then setting the selected COx values to positive one reduces the likelihood that the selected COx values will pull a mean COx value below the threshold level.

Figure 7A:
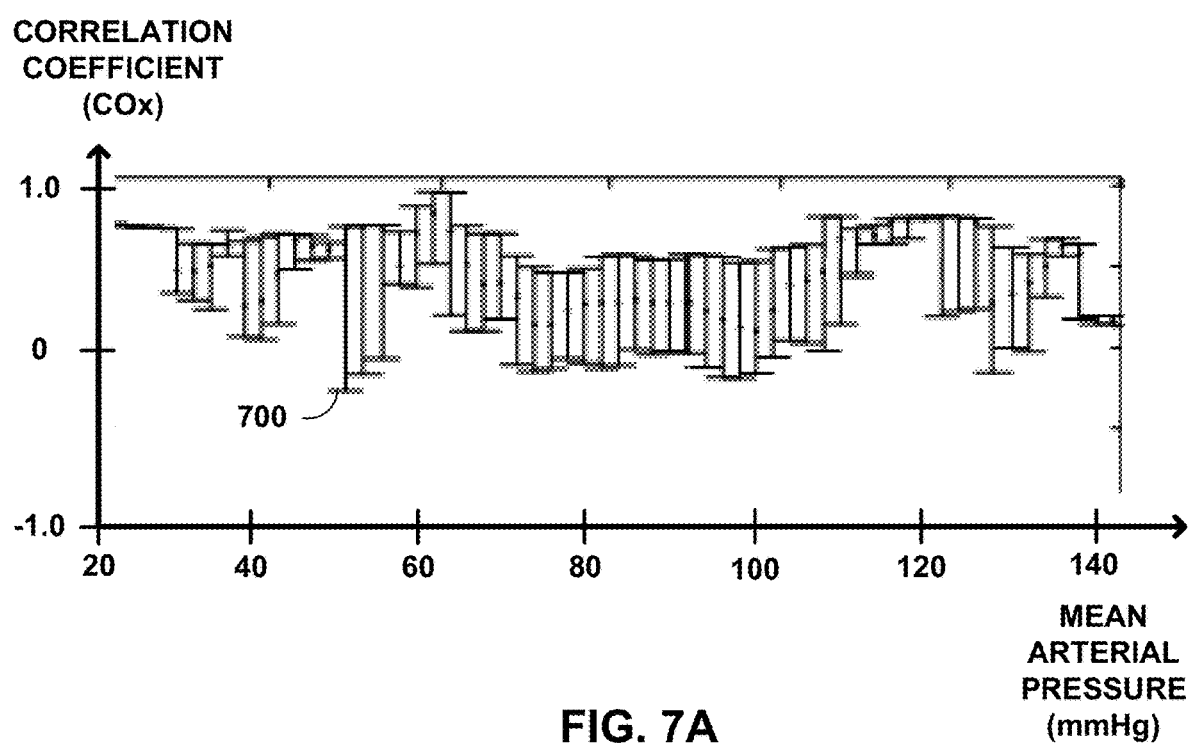
FIG. 7A is an example graph illustrating bins of correlation coefficient values without updated values versus mean arterial pressure.
Figure 7B:
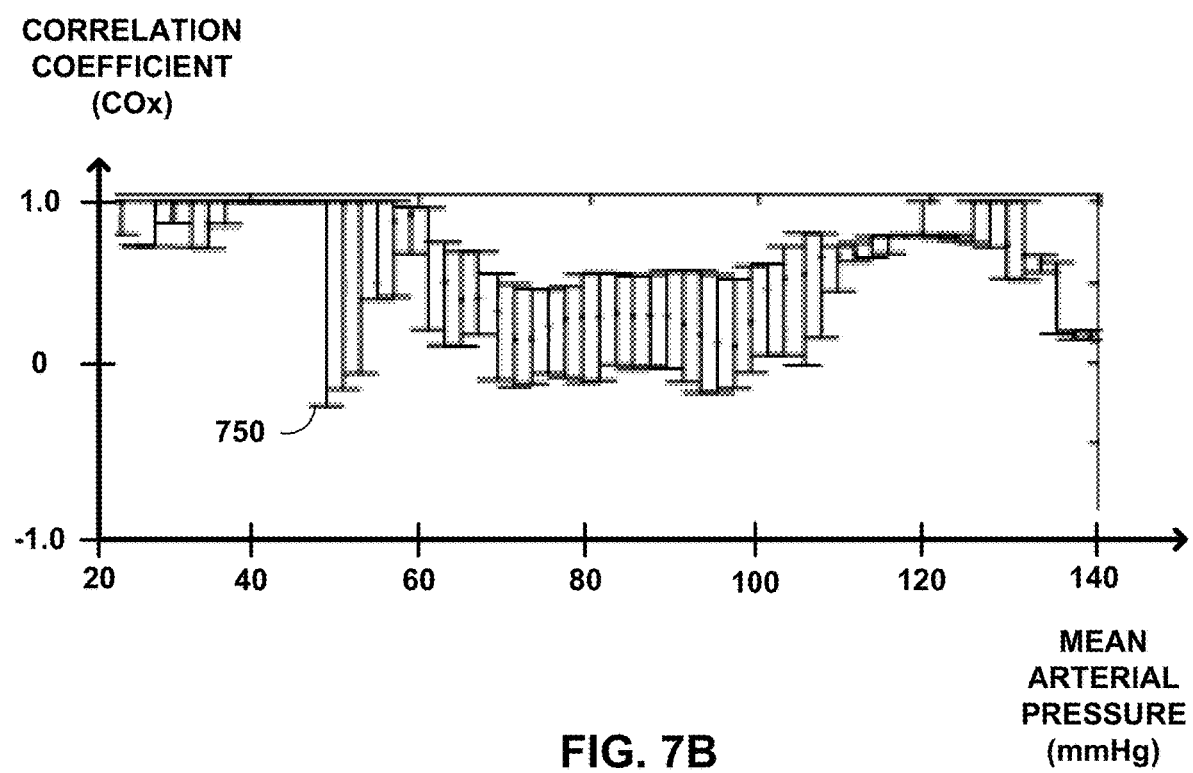
FIG. 7B is an example graph illustrating bins of correlation coefficient values with updated values versus mean arterial pressure.

FIG. 7A is an example graph illustrating bins of COx values without updated values versus mean arterial pressure. Processing circuitry 110 presents the graphic elements (e.g., error bars) of FIG. 7A to represent the data points shown in FIGS. 4 and 5. FIG. 7B is an example graph illustrating bins of COx values with updated values versus mean arterial pressure. Processing circuitry 110 presents the graphic elements of FIG. 7B to represent the data points shown in FIG. 6. The graph of FIG. 7B shows a distinct tightening of the bins at the higher and lower MAP values, and thus an easier identification of the limits of autoregulation.

Each graphic element includes an error bar that represents a data bin or data bucket, where a bin is a group of COx values that are associated with similar MAP values. The dot near the middle of each error bar represents the mean, average, weighted average, or median of the COx values in the bin. The upper line and the lower line of each error bar can represent the minimum and maximum COx values in the bin. The upper line and the lower line of each error bar can indicate standard deviations and/or percentiles (e.g., 25th and 75th percentiles) of the correlation coefficient values in a bin.

Processing circuitry 110 presents graphic element 700 shown in FIG. 7A based on the COx values associated with MAP values between 48 and 50 mmHg. After determining updated values for selected COx values associated with MAP values between 48 and 50 mmHg, processing circuitry 110 presents graphic element 750. The lower line of graphic element 700 is equal to the lower line of graphic element 750. The upper line of graphic element 700 is approximately 0.8, while the upper line of graphic element 750 is equal to positive one. Thus, processing circuitry 110 has determined an updated value of positive one for at least one selected COx value in the bin associated with graphic element 750.

In the graph of FIG. 7A, some of the graphic elements plotted at low MAP values to the left of graphic element 700 indicate that the mean COx values are less than 0.5. However, after processing circuitry 110 determines updated values for selected COx values, as shown in FIG. 7B, the symbols plotted at low MAP values to the left of graphic element 750 indicate that the mean COx values are greater than 0.5. If processing circuitry 110 determines an estimate of the lower limit of autoregulation based on determining the lowest bin at which the mean COx value of the bin is less than a threshold value (e.g., 0.5 or 0.7), processing circuitry 110 may determine an incorrectly low estimate based on the data bins shown in FIG. 7A. However, using the data bins shown in FIG. 7B, processing circuitry 110 may determine an estimate of the lower limit of autoregulation at 50 or 55 mmHg.

Figure 8:
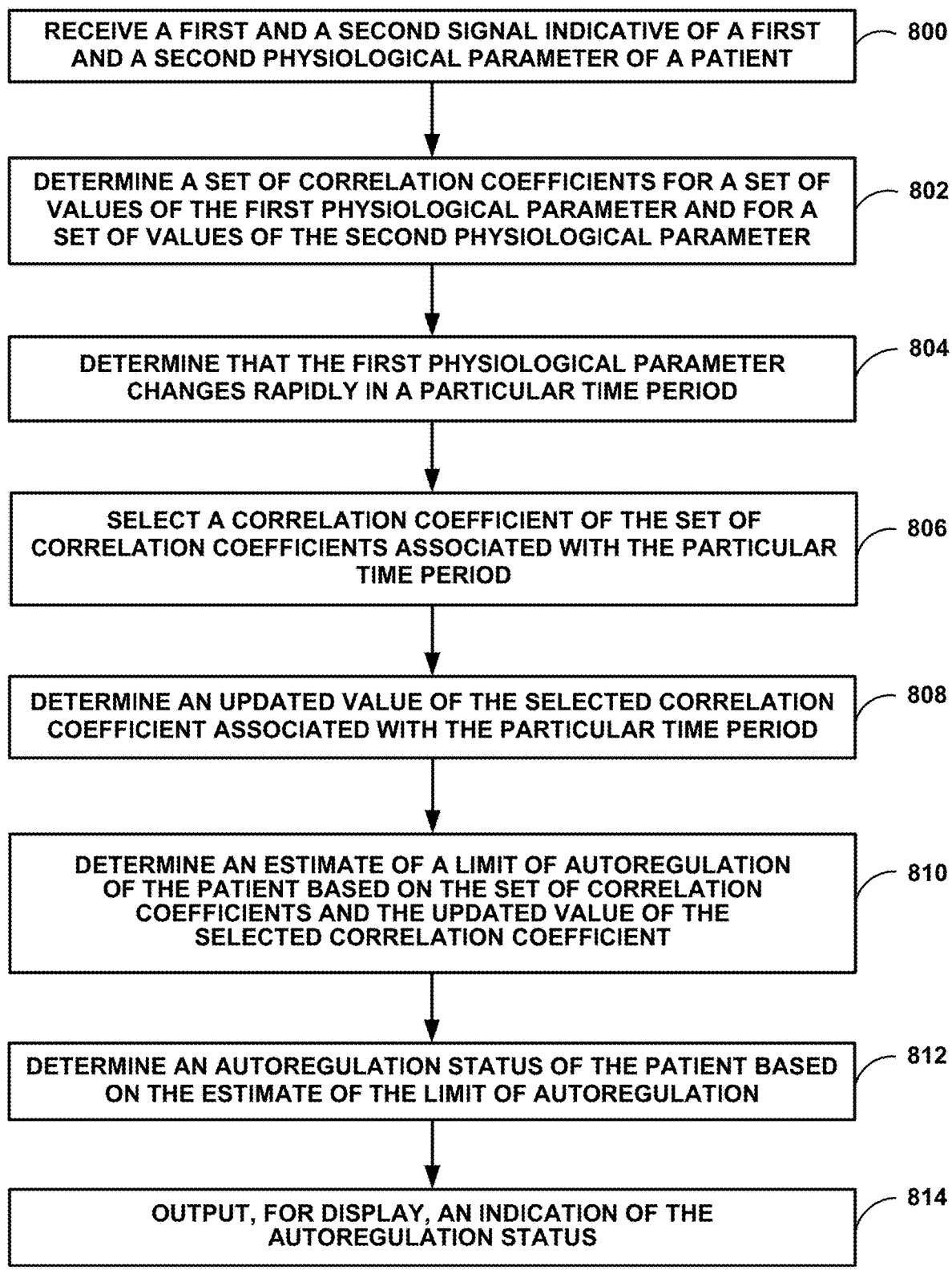
FIG. 8 is a flow diagram illustrating example techniques for determining changes in autoregulation, in accordance with some examples of this disclosure.

FIG. 8 is a flow diagram illustrating example techniques for determining changes in autoregulation, in accordance with some examples of this disclosure. Although FIG. 8 is described with respect to processing circuitry 110 of regional oximetry device 100 (FIG. 1), in other examples, processing circuitry 210,214, and/or 216 (FIG. 2), alone or in combination with processing circuitry 110, may perform any part of the techniques of FIG. 8.

In the example of FIG. 8, processing circuitry 110 receives a first signal indicative of a first physiological parameter of a patient and a second signal indicative of a second physiological parameter of the patient (800). In some examples, processing circuitry 110 receives signals directly from sensing devices 150-152. Additionally or alternatively, processing circuitry 110 receives signals from sensing circuitry 140-142, where sensing circuitry 140-142 may preprocess the physiological signals before delivering the signals to processing circuitry 110.

In the example of FIG. 8, processing circuitry 110 determines a set of correlation coefficient values for a set of values of the first physiological parameter and for a set of values of the second physiological parameter (802). Processing circuitry 110 may determine each correlation coefficient, for example, as a Pearson's coefficient for the two physiological parameters. Each correlation coefficient value may indicate the linear correlation between the two physiological parameters at a particular time or over a particular window of time (e.g., a sampling window). In some examples, processing circuitry 110 may determine the linear correlation between the two physiological parameters over a sampling window of five seconds or ten seconds.

In the example of FIG. 8, processing circuitry 110 determines that the first physiological parameter changes rapidly in a particular time period (804). For example, processing circuitry 110 can determine a rapid change in the first physiological parameter in response to determining that a rate of change of the first physiological parameter exceeds a first threshold rate, determining that a rate of change of the correlation coefficient values exceeds a second threshold rate, and/or determining that a product of the first physiological parameter and the correlation coefficient values exceeds a third threshold rate. In some examples, the third threshold rate is less than a product of the first threshold rate and the second threshold rate.

Processing circuitry 110 may not necessarily directly determine that the first physiological parameter changes rapidly. Instead, processing circuitry 110 may be configured to determine that the first physiological parameter changes rapidly by inferring or guessing that the first physiological parameter changes rapidly in a particular time period. Processing circuitry 110 can infer or guess a rapid change based on a rate of change of the correlation coefficient values and/or a rate of change of a product of the first physiological parameter and the correlation coefficient values. Additionally or alternatively, processing circuitry 110 may also use a rate of change of the second physiological parameter or a rate of change of a product of the first physiological parameter and the second physiological parameter, and/or other metric(s), to infer a rapid change in a physiological parameter.

Some patients may have physiological parameters that changes at faster rates than other patients. A rate of change of two mmHg per second may indicate a higher likelihood of error for a first patient, but not for a second patient. Processing circuitry 110 may determine threshold rates based on a parametric study of historical data at least in part by dynamically determining the threshold rate for a given patient based on previously determined values of the first physiological parameter of the patient. For example, processing circuitry 110 may select the threshold rate such that a percentage of values of the first physiological parameter are determined to be rapidly changing. The percentage may be ten percent, five percent, two percent, or one percent of all of the previously determined values of the first physiological parameter.

In the example of FIG. 8, processing circuitry 110 then selects a correlation coefficient value associated with the particular time period in response to determining that the first physiological parameter changes rapidly in a particular time period (806). When processing circuitry 110 determines a set of correlation coefficient values, processing circuitry 110 may associated each correlation coefficient value with a time period. For example, if processing circuitry 110 determines ten correlation coefficient values per second, each correlation coefficient values may be offset in time from an adjacent correlation coefficient value by one hundred milliseconds.

In the example of FIG. 8, processing circuitry 110 determines an updated value of the selected correlation coefficient value associated with the particular time period in response to determining that the first physiological parameter changes rapidly in a particular time period (808). Processing circuitry 110 can determine updated values at least in part by setting updated values of positive one for the selected correlation coefficient values. Setting the selected correlation coefficient values to one may reduce the likelihood that the selected correlation coefficient values will introduce error into the determination of autoregulation status.

In some examples, processing circuitry 110 is configured to determine updated values for some or all of the correlation coefficient values in the set of correlation coefficient values in response to determining that the first physiological parameter changes rapidly. Thus, the rapid change in the first physiological parameter may be a trigger for processing circuitry 110 to set updated values. After determining the rapid change, processing circuitry 110 may retrospectively (e.g., after an end of a window of time) alter the curve of correlation coefficient values (e.g., as shown in the graphs of FIGS. 4-7B).

In some examples, processing circuitry 110 may alternatively or additionally be configured to determine or seek out suspicious data points (e.g., correlation coefficient values) that have the characteristic of rapid change. Processing circuitry 110 may then be configured to assess the suspicious data points for correction based on the changes in the values of the first physiological parameter, the values of the second physiological parameter, the correlation coefficient values, and/or the product of any two of these values. Once processing circuitry 110 reaches the end of a window of time, where the first physiological parameter or the correlation coefficient values have changed rapidly, processing circuitry 110 can alter some or all of the correlation coefficient values based on determining that the values of one or more parameters have changed significantly within the window of time.

In the example of FIG. 8, processing circuitry 110 determines an estimate of a limit of autoregulation of the patient based on the set of correlation coefficient values and the updated value of the selected correlation coefficient value (810). Processing circuitry 110 may use an algorithm (e.g., finding the lowest bin having a metric below a threshold level) to determine an estimate of the lower limit of autoregulation. For example, processing circuitry 110 may determine the lowest value of the first physiological parameter that is associated with a bin having an average correlation coefficient value that is less than a threshold level, such as 0.8, 0.7, 0.6, 0.5, 0.4, 0.3, 0.2, 0.1, or 0.0. To determine an estimate of the upper limit of autoregulation, processing circuitry 110 may determine the highest value of the first physiological parameter that is associated with a bin having an average correlation coefficient value that is greater than a threshold level.

In the example of FIG. 8, processing circuitry 110 determines an autoregulation status of the patient based on the estimate of the limit of autoregulation (812). Processing circuitry 110 can determine the autoregulation status at least in part by determining whether the current MAP value of the patient is greater than the estimate of the lower limit of autoregulation and/or less than the estimate of the upper limit of autoregulation.

In the example of FIG. 8, processing circuitry 110 outputs, for display via display 132, an indication of the autoregulation status (814). Processing circuitry 110 can cause display 132 to present one or more of the indicators 310, 320, 330, 340, 350, 360, and 370. For example, processing circuitry 110 can cause display 132 to present autoregulation status indicator 350, which may include text or a color representative of an impaired or intact autoregulation status.

Processing circuitry 110 may also use the techniques of this disclosure to determine that a first physiological parameter changes rapidly based on HVx values, PRx values, and/or Mx values, rather than just COx values, using the techniques described herein. For example, in step 802, processing circuitry 110 can determine a set of HVx values, PRx values, and/or Mx values. In steps 806 and 808, processing circuitry 110 can select an HVx value, a PRx value, and/or an Mx value associated with a particular time period and determine an updated value of the selected HVx value, the selected PRx value, and/or the Mx value.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150-152 and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

Where processing circuitry 110 is described herein as determining that a value is less than or equal to another value, this description may also include processing circuitry 110 determining that a value is only less than the other value. Similarly, where processing circuitry 110 is described herein as determining that a value is less than another value, this description may also include processing circuitry 110 determining that a value is less than or equal to the other value.

The same properties may also apply to the terms "greater than" and "greater than or equal to."

Various examples of the disclosure have been described. Any combination of the described systems, operations, or functions is contemplated. These and other examples are within the scope of the following claims.

What is claimed is:

1. A device comprising:
a display; and
processing circuitry configured to:
receive a first signal indicative of a first physiological parameter of a patient;
receive a second signal indicative of a second physiological parameter of the patient;
determine a set of correlation coefficient values that correlate values from a set of values of the first physiological parameter to values from a set of values of the second physiological parameter;
determine that the first physiological parameter changes rapidly in a particular time period;
in response to determining that the first physiological parameter changes rapidly in the particular time period:
select a correlation coefficient value from the set of correlation coefficient values, the selected correlation coefficient value being associated with the particular time period; and
determine an updated value of the selected correlation coefficient value;
determine an estimate of a limit of autoregulation of the patient based on the set of correlation coefficient values and the updated value of the selected correlation coefficient value;
determine an autoregulation status of the patient based on the estimate of the limit of autoregulation; and
output, for display via the display, an indication of the autoregulation status.

2. The device of claim 1, wherein the processing circuitry is configured to determine that the first physiological parameter changes rapidly in the particular time period at least in part by determining that a rate of change of the first physiological parameter in the particular time period exceeds a threshold rate.

3. The device of claim 2, wherein the processing circuitry is further configured to dynamically determine the threshold rate based on previously determined values of the first physiological parameter.

4. The device of claim 1, wherein the processing circuitry is configured to determine that the first physiological parameter changes rapidly in the particular time period at least in part by determining that a rate of change of the correlation coefficient values in the particular time period exceeds a threshold rate.

5. The device of claim 4, wherein the processing circuitry is further configured to dynamically determine the threshold rate based on previously determined correlation coefficient values.

6. The device of claim 1, wherein the processing circuitry is configured to determine that the first physiological parameter changes rapidly in the particular time period at least in part by determining that a product of the rate of change of the first physiological parameter and a rate of change of the correlation coefficient values in the particular time period exceeds a threshold rate.

7. The device of claim 1, wherein the processing circuitry is configured to determine the updated value of the selected correlation coefficient value at least in part by setting a value of the selected correlation coefficient value to one.

8. The device of claim 1, wherein the processing circuitry is configured to determine the estimate of the limit of autoregulation based on a window having a length of time, wherein the processing circuitry is further configured to shorten the length of time of the window in response to determining that the first physiological parameter changes rapidly in the particular time period.

9. The device of claim 8, wherein the processing circuitry is further configured to determine a new length of time for the window based on a rate of change of the first physiological parameter in the particular time period.

10. The device of claim 8, wherein the processing circuitry is further configured to determine a new length of time for the window based on a rate of change of correlation coefficient values in the particular time period.

11. The device of claim 1, wherein the processing circuitry is configured to determine updated values for the set of correlation coefficient values in response to determining that the first physiological parameter changes rapidly in the particular time period.

12. The device of claim 1,
wherein the processing circuitry is configured to determine the set of correlation coefficient values during a window of time,
wherein the processing circuitry is configured to determine the estimate of the limit of autoregulation based on the set of correlation coefficient values during the window of time, and
wherein the processing circuitry is configured to, after an end of the window of time, select the correlation coefficient associated with the particular time period and determine an updated value of the selected correlation coefficient.

13. The device of claim 1,
wherein the processing circuitry is further configured to determine that a value of the first physiological parameter associated with the particular time period is less than a threshold value of the first physiological parameter, and
wherein the processing circuitry is configured to determine the updated value of the selected correlation coefficient value in response to determining that the value of the first physiological parameter associated with the particular time period is less than the threshold value.

14. The device of claim 1,
wherein the processing circuitry is configured to determine the estimate of the limit of autoregulation at least in part by determining an estimate of a lower limit of autoregulation,
wherein the processing circuitry is further configured to determine that a value of the first physiological parameter associated with the particular time period is less than the estimate of the lower limit of autoregulation, and
wherein the processing circuitry is configured to determine the updated value of the selected correlation coefficient value in response to determining that the value of the first physiological parameter associated with the particular time period is less than the estimate of the lower limit of autoregulation.

15. A method comprising:
receiving, by processing circuitry of a device and from sensing circuitry of the device, a first signal indicative of a first physiological parameter of a patient;

receiving, by the processing circuitry and from the sensing circuitry, a second signal indicative of a second physiological parameter of the patient;

determining, by the processing circuitry, a set of correlation coefficient values that correlate values from a set of values of the first physiological parameter to values from a set of values of the second physiological parameter;

determining, by the processing circuitry, that the first physiological parameter changes rapidly in a particular time period;

in response to determining that the first physiological parameter changes rapidly in particular time period:

selecting, by the processing circuitry, a correlation coefficient value from the set of correlation coefficient values, the selected correlation coefficient value being associated with the particular time period; and determining, by the processing circuitry, an updated value of the selected correlation coefficient value;

determining, by the processing circuitry, an estimate of a limit of autoregulation of the patient based on the set of correlation coefficient values and the updated value of the selected correlation coefficient value;

determining, by the processing circuitry, an autoregulation status of the patient based on the estimate of the limit of autoregulation; and outputting, by the processing circuitry for display, an indication of the autoregulation status.

16. The method of claim 15, wherein determining that the first physiological parameter changes rapidly in the particular time period comprises determining that a rate of change of the first physiological parameter in the particular time period exceeds a threshold rate.

17. The method of claim 15, wherein determining that the first physiological parameter changes rapidly in the particular time period comprises determining that a rate of change of the correlation coefficient values in the particular time period exceeds a threshold rate.

18. The method of claim 15, wherein determining that the first physiological parameter changes rapidly in the particular time period comprises determining that a rate of change of the first physiological parameter in the particular time period exceeds a threshold rate.

19. A device comprising:
processing circuitry configured to:
receive a first signal indicative of a first physiological parameter of a patient;
receive a second signal indicative of a second physiological parameter of the patient;
determine that the first physiological parameter changes rapidly;
in response to determining that the first physiological parameter changes rapidly, shorten a length of time of a window in which to determine a set of correlation coefficient values that correlate values from a set of values of the first physiological parameter to values from a set of values of the second physiological parameter;
determine an estimate of a limit of autoregulation of the patient based on the set of correlation coefficient values;
determine an autoregulation status of the patient based on the estimate of the limit of autoregulation; and
output, for display, an indication of the autoregulation status.

20. The device of claim 19, wherein the processing circuitry is further configured to determine a new length of time for the window based on at least one of a rate of change of the first physiological parameter or a rate of change of the correlation coefficient values.

* * * * *